US 11,835,454 B2

(12) United States Patent
Narisada et al.

(10) Patent No.: US 11,835,454 B2
(45) Date of Patent: Dec. 5, 2023

(54) LIQUID TRANSFER MONITORING METHOD AND SAMPLE MEASURING DEVICE

(71) Applicant: SYSMEX CORPORATION, Kobe (JP)

(72) Inventors: Noriyuki Narisada, Kobe (JP); Yasunori Maekawa, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 269 days.

(21) Appl. No.: 17/038,431

(22) Filed: Sep. 30, 2020

(65) Prior Publication Data

US 2021/0096072 A1    Apr. 1, 2021

(30) Foreign Application Priority Data

Sep. 30, 2019   (JP) .................. 2019-180011

(51) Int. Cl.
  *G01N 21/53* (2006.01)
  *G01N 33/487* (2006.01)
  *G01N 21/88* (2006.01)
  *B01L 3/00* (2006.01)
  *G06T 7/11* (2017.01)
  (Continued)

(52) U.S. Cl.
  CPC ........ *G01N 21/53* (2013.01); *B01L 3/502715* (2013.01); *G01N 21/8851* (2013.01);
  (Continued)

(58) Field of Classification Search
  CPC .. G01N 21/53; G01N 21/8851; G01N 33/487; G06T 7/136; G06T 7/11;
  (Continued)

(56) References Cited

U.S. PATENT DOCUMENTS

2009/0091756 A1*  4/2009  Yamaguchi ........ G01N 15/0205
                                                 356/336
2012/0287434 A1   11/2012  Burghardt et al.
(Continued)

FOREIGN PATENT DOCUMENTS

JP    S57-149949 A    9/1982
JP    H06-94724 A     4/1994
(Continued)

OTHER PUBLICATIONS

The extended European search report dated Jan. 29, 2021 in a counterpart European patent application No. 20197182.7.
(Continued)

*Primary Examiner* — Jamil Ahmed
(74) *Attorney, Agent, or Firm* — Crowell & Moring LLP

(57) ABSTRACT

A liquid transfer monitoring method to monitor a transfer state of a liquid such as a sample or a reagent having a high transparency which transmits light is provided. The liquid transfer monitoring method comprises a step of transferring a liquid 30 held in a first liquid holding portion 21 to a second liquid holding portion 22 connected to the first liquid holding portion 21, a step of acquiring information 40 relating to a scattered light intensity obtained by irradiating light 91 on the irregular inner surface 23 of at least one of the first liquid holding portion 21 and the second liquid holding portion 22 after starting the transfer of the liquid 30, and a step of monitoring the liquid transfer to the second liquid holding portion 22 based on the information 40 relating to the intensity of scattered light.

20 Claims, 19 Drawing Sheets

(51) Int. Cl.
*G06T 7/136* (2017.01)
*G06T 7/00* (2017.01)
*H04N 23/56* (2023.01)

(52) U.S. Cl.
CPC ......... *G01N 33/487* (2013.01); *G06T 7/0016* (2013.01); *G06T 7/11* (2017.01); *G06T 7/136* (2017.01); *B01L 2300/0627* (2013.01); *H04N 23/56* (2023.01)

(58) Field of Classification Search
CPC ............. G06T 7/0016; B01L 3/502715; B01L 2300/0627; H04N 5/2256
See application file for complete search history.

(56) References Cited

U.S. PATENT DOCUMENTS

| | | | |
|---|---|---|---|
| 2018/0136243 A1 | 5/2018 | Boehm et al. | |
| 2018/0207634 A1* | 7/2018 | Butzkuven | ............ G01F 23/292 |

FOREIGN PATENT DOCUMENTS

| | | | | |
|---|---|---|---|---|
| JP | H07-181126 A | | 7/1995 | |
| JP | 2003-004752 A | | 1/2003 | |
| JP | 2008-003074 A | | 1/2008 | |
| JP | 2009-257988 A | | 11/2009 | |
| JP | 2011-137673 A | | 7/2011 | |
| JP | 2012-185810 A | | 9/2012 | |
| JP | 2018109526 A | * | 7/2018 | ............. G01R 33/26 |
| WO | 2015/151240 A1 | | 10/2015 | |
| WO | WO-2015151240 A1 | * | 10/2015 | ........... G01N 21/532 |

OTHER PUBLICATIONS

Communication pursuant to Article 94(3) EPC, dated Aug. 25, 2022, pp. 1-5, in European patent application No. 20197182.7, European Patent Office, Munich, Germany.

Japanese Office Action dated Jun. 27, 2023 in a counterpart Japanese patent application No. 2019-180011.

* cited by examiner

Abnormality process example

| Interrupt measurement |
| Notify user during measurement |
| Display abnormality notice in measurement result on display unit |

LIQUID TRANSFER MONITORING METHOD AND SAMPLE MEASURING DEVICE

RELATED APPLICATIONS

This application claims priority to Japanese Patent Application No. 2019-180011, filed on Sep. 30, 2019, the entire content of which is incorporated herein by reference.

BACKGROUND OF THE INVENTION

1. Field of the Invention

The present invention relates to a liquid transfer monitoring method and a sample measuring device for monitoring the transfer state of a liquid transported in a flowpath.

2. Description of the Related Art

Japanese Unexamined Patent Publication No. 2009-257988 discloses an examination apparatus 900 including an imaging unit 902 for imaging the flow path of a microchip 901, as shown in FIG. 26. The imaging unit 902 includes a lens 903 and an illumination unit 904, and optically detects a sample flowing through the flow path of the microchip 901. In this way the sample passing through the monitoring area of the microchip 901 is subjected to image processing to analyze the liquid transfer state.

SUMMARY OF THE INVENTION

Although the imaging unit 902 images the sample flowing in the flow path of the microchip 901 to monitor the liquid transfer state in Japanese Unexamined Patent Publication No. 2009-257988, it is difficult to image and monitor a highly transparent sample such as plasma or serum, or a liquid such as a reagent.

When transferring a liquid such as a highly transparent sample of plasma or serum, or a reagent through the flow path, the transfer purpose may not be achieved if a transfer failure such as a failure in the measured quantity of the liquid or a failure in transferring the liquid to a predetermined liquid holding portion occurs. Therefore, it is desirable to be able to monitor the liquid transfer state even with a highly transparent liquid that transmits light.

The present invention allows monitoring of the transfer state of a liquid such as a highly transparent sample or reagent that transmits light.

In order to achieve this goal, as shown in FIG. 1, the present invention is a liquid transfer monitoring method for monitoring the transfer state of a liquid (30) transferred in a flow path (10) having at least two liquid holding portions (20) and used in a sample measuring device, wherein the method includes a step of transferring the liquid (30) held in the first liquid holding portion (21) to a second liquid holding portion (22) connected to the first liquid holding portion (21), a step of acquiring information (40) related to scattered light intensity obtained by irradiating light (91) on an irregular inner surface (23) of at least one of the first liquid holding portion (21) and the second liquid holding portion (22) after the transfer of the liquid (30) is started; and a step of monitoring the liquid transfer to the second liquid holding portion (22) based on the information (40) related to the scattered light intensity.

In the liquid transfer monitoring method according to the present invention described above, the light (91) is irradiated on the irregular inner surface of at least one of the first liquid holding portion (21) and the second liquid holding portion (22) to obtain information (40) related to the scattered light intensity. When the liquid holding portion (20) is filled with air without the liquid (30), the irradiated irregular inner surface (23) scatters the irradiated light (91) in random directions. On the other hand, when the liquid holding portion (20) is filled with the liquid (30), the irregularity of the inner surface (23) is covered with the liquid (30) and the difference in the refractive index is reduced and the light scattering is suppressed. Since the information (40) related to the scattered light intensity varies depending on the presence or absence of the liquid (30) as described above, it is possible to grasp whether the liquid (30) is being transferred to the liquid holding portion (20), and how far the liquid (30) is being transferred based on the obtained information (40) related to the scattered light intensity. In this way the liquid transfer state can be monitored even for liquids such as highly transparent samples and reagents that transmit light.

The sample measuring device (100) according to the present invention is a sample measuring device that transfers a liquid (30) to a flow path (10) having at least two liquid holding portions (20) and performs measurement using the liquid (30), as shown in FIG. 1, the sample measuring device (100) includes a liquid feeding unit (110) that applies an external force to the liquid (30) held in the first liquid holding portion (21) and transfers the liquid (30) to the second liquid holding portion (22) connected to the first liquid holding portion (21), an illumination unit (120) that irradiates light (91) on the irregular inner surface (23) of at least one of the first liquid holding portion (21) and the second liquid holding portion (22), a photodetection unit (130) for detecting scattered light (92) originating from light (91) irradiated on the inner surface (23), a control unit (140) for performing controls to acquire information (40) related to scattered light intensity based on signals from the photodetection unit (130) and determine a presence or absence of a liquid (30) within a liquid holding portion (20) based on the information (40) related to the scattered light, and a measurement unit (145) that performs measurement using the liquid (30).

In the sample measuring device (100) according to the present invention, since the information (40) regarding the scattered light intensity varies depending on the presence or absence of the liquid (30) in the liquid holding portion (20) similar to the above-described liquid transfer monitoring method, the control unit (140) determines whether the liquid (30) is being transferred to the liquid holding portion (20), and how far the liquid (30) is being transferred based on the acquired information (40) related to the scattered light intensity, and this status can be grasped by a user. In this way the liquid transfer state can be monitored even for liquids such as highly transparent samples and reagents that transmit light.

According to the present invention, the liquid transfer state can be monitored even for liquids such as samples and reagents that have high transparency and transmit light.

DETAILED DESCRIPTION OF THE PREFERRED EMBODIMENTS

Hereinafter, embodiments will be described with reference to the drawings.

Liquid Transfer Monitoring Method Summary

A summary of the liquid transfer monitoring method according to the present embodiment will be described with reference to FIGS. 1 to 4.

Figure 1:
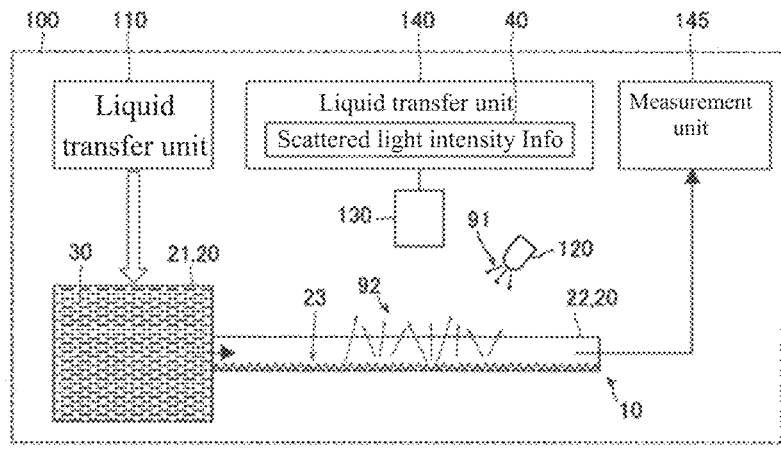
FIG. 1 is a schematic diagram describing a liquid transfer monitoring method and a sample measuring device according to an embodiment.

As shown in FIG. 1, the liquid transfer monitoring method of the present embodiment is a method of monitoring the transfer state of a liquid 30 transferred in a flow path 10 having at least two liquid holding portions 20.

The liquid 30 is a liquid used in the sample measuring device. The liquid can be a sample or reagent. When the liquid 30 is a sample, the liquid 30 is, for example, a biological sample collected from a human being who is a subject. The liquid 30 may be blood, urine, bodily fluid, or other sample. The blood sample can be whole blood, serum, plasma and the like. The liquid 30 is mainly composed of a liquid and may include a solid component such as cells. The liquid 30 is, for example, a highly transparent liquid. Examples of such liquids are serum or plasma, urine, tissue fluid and the like. The liquid 30 may be a reagent used for measuring a sample. The reagent may be, for example, a labeling reagent, an enzyme reagent, a washing solution, a buffer solution or the like.

The flow path 10 is a hollow space through which the liquid 30 can flow. The flow channel 10 has one or more inner surfaces and is formed in a tubular shape or a groove shape. Depending on the cross-sectional shape of the flow channel 10, the inner surface can be provided as a single surface if the flow channel 10 has a circular cross section, or provided as the same number of surfaces as the number of sides if the flow channel 10 has a polygonal shape.

The liquid holding portion 20 is an empty space having a volume capable of containing a predetermined amount of liquid 30. The liquid holding portion 20 is a space in which the liquid 30 can be stored and has, for example, an inner bottom surface and one or more inner side surfaces. The liquid holding portion 20 also may be a space that has an inner upper surface and is closed off from the outside. The liquid holding portion 20 includes a first liquid holding portion 21 and a second liquid holding portion 22. The first liquid holding portion 21 and the second liquid holding portion 22 are in fluid communication with each other in the flow path 10.

In the present embodiment, at least one of the first liquid holding portion 21 and the second liquid holding portion 22 includes the irregular inner surface 23. Both the first liquid holding portion 21 and the second liquid holding portion 22 also may have an inner surface 23 having irregularities. In other words, the inner surface 23 having irregularities is a roughened surface. The inner surface 23 is a surface including random fine irregularities. In this specification, the irregular inner surface 23 is a surface that scatters light in random directions. The irregular inner surface 23 has a surface roughness of, for example, 1.3 μm or more and 6.9 μm or less. The surface roughness is an arithmetic mean roughness.

The irregular inner surface 23 is formed by etching or the like when the hollow liquid holding portion 20 is formed on an object. The irregular inner surface 23 may be formed by a roughening treatment after the liquid holding portion 20 is formed. The irregular inner surface 23 may be any one of the inner bottom surface, the inner side surface, and the inner upper surface of the liquid holding portion 20, or may be the entire inner surface.

Figure 2:
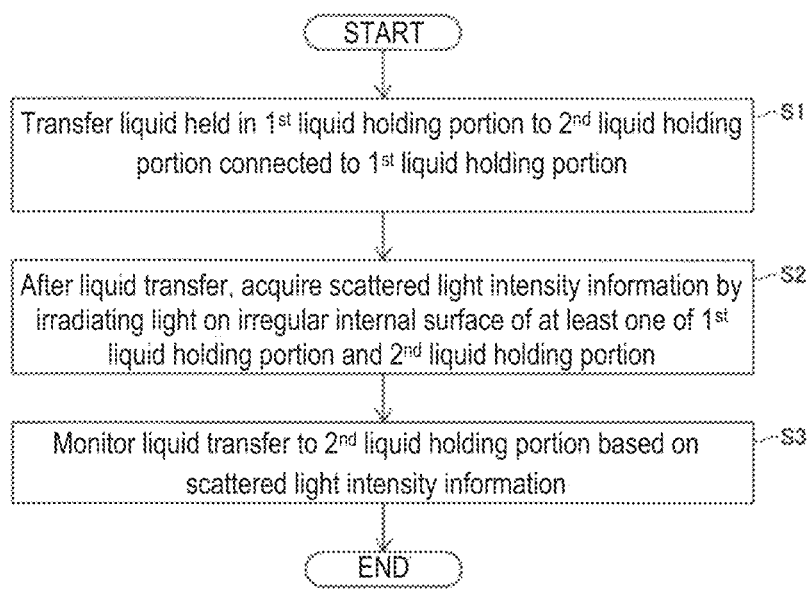
FIG. 2 is a flowchart illustrating a liquid transfer monitoring method.

As shown in FIG. 2, the liquid delivery monitoring method of this embodiment includes the following steps S1 to S3.

(S1) A step of transferring a liquid 30 held in the first liquid holding portion 21 to a second liquid holding portion 22 connected to the first liquid holding portion 21.

(S2) A step of acquiring information related to scattered light intensity obtained by irradiating light 91 on an irregular inner surface 23 of at least one of the first liquid holding portion 21 and the second liquid holding portion 22 after the transfer of the liquid 30 is started; and (S3) A step of monitoring the liquid transfer to the second liquid holding portion 22 based on the information 40 related to the scattered light intensity.

In step S1, the liquid 30 moves in the flow path 10 by the action of an external force, for example. The external force is, for example, a capillary force. The external force is, for example, pressure. The pressure may be either air pressure or water pressure. The external force is, for example, centrifugal force.

In step S2, the illumination unit 120 irradiates a light 91 on the irregular inner surface 23. FIG. 1 shows an example in which the irregular inner surface 23 is formed on the second liquid holding portion 22, and the inner surface 23 of the second liquid holding portion 22 is irradiated with light 91. The irregular inner surface 23 also may be formed on the first liquid holding portion 21, and the inner surface 23 of the first liquid holding portion 21 may be irradiated with the light 91, or the first liquid holding portion 21 and the second liquid holding portion 22 such that the light 91 may be irradiated on both inner surfaces 23 of the liquid holding portions 21 and 22.

Light 91 is scattered on the irregular inner surface 23, and the scattered light 92 generated from the inner surface 23 travels in random directions. The scattered light 92 from the inner surface 23 is detected by the photodetection unit 130. The illumination unit 120 includes a light source such as an LED (light emitting diode), a laser light source, and other lamps. The photodetection unit 130 includes, for example, an optical sensor such as a photodiode and a photomultiplier tube, an image sensor, and the like. Information 40 related to the scattered light intensity is acquired from the signal of the light detection unit 130.

The information 40 related to the scattered light intensity is information that allows the magnitude of the scattered light intensity to be comprehended. The information 40 related to the scattered light intensity may be the scattered light intensity itself. The information 40 related to the scattered light intensity also may be an index or an index that is acquired by analyzing the signal of the photodetection unit 130 and expresses the magnitude of the scattered light intensity.

In step S3, liquid transfer is monitored based on the information 40 related to the scattered light intensity. The monitoring of the liquid transfer is performed to collect information on the movement of the liquid 30. Monitoring the liquid transfer includes, for example, detecting the liquid 30 moving in the flow path 10. Monitoring the liquid transfer may include discovering undesirable conditions related to liquid transfer. The undesirable condition regarding the liquid transfer is, for example, the inclusion of air when the liquid 30 is metered, the liquid 30 remains in the flow path 10 and the like. Monitoring the liquid transfer includes, for example, monitoring the ratio of air originally mixed in the liquid 30. The monitoring of the liquid transfer includes, for example, monitoring the ratio of air mixed in the liquid 30 during the liquid transfer.

Steps S2 and S3 can be performed during or after the liquid transfer in step S1. The monitoring of the liquid transfer is not only real-time monitoring during liquid transfer, but it also is possible to know afterwards that the liquid transfer was performed properly by comparing the information before and after the liquid transfer.

Figure 3:
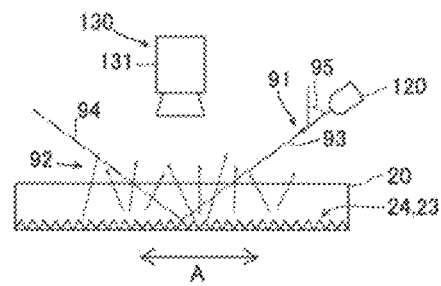
FIG. 3 is a schematic diagram showing a liquid holding portion in an empty state without liquid.

Specifically, the monitoring of the liquid transfer can be performed based on the difference in the information 40 related to the scattered light intensity. That is, as shown in FIG. 3, when the liquid 30 is not present in the liquid holding portion 20 and the liquid holding portion 20 is filled with air, the irradiated light 91 is scattered by the irregular inner surface 23 to generated scattered light 92 in random directions. Therefore, the scattered light intensity is detected at a relatively high level.

Figure 4:
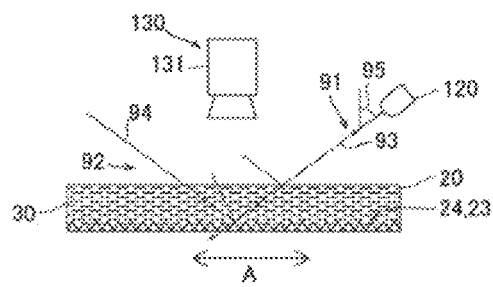
FIG. 4 is a schematic diagram showing a liquid holding portion in a state of containing liquid.

On the other hand, as shown in FIG. 4, when the liquid holding portion 20 is filled with the liquid 30, the irregularity of the inner surface 23 is covered with the liquid 30 and the difference in the refractive index is reduced, so that light scattering is suppressed. That is, the amount of light that is spectrally reflected by the surface of the liquid 30 that covers the inner surface 23, or is transmitted or absorbed without being scattered by the inner surface 23 even if it is transmitted through the surface of the liquid 30, increases and the intensity of scattered light decreases. Therefore, the scattered light intensity is detected at a relatively low level. As a result, it is possible to distinguish the region where the liquid 30 is present and the region where the liquid 30 is not present in the flow path 10. The relatively high or low here is the relative level when comparing the case where the liquid 30 does not exist in the liquid holding portion 20 and the case where the liquid holding portion 20 is filled with the liquid 30.

Note that the object in which the flow path 10 is formed is made of a resin material, metal, glass, or other substance, and has a refractive index different from the refractive index of air. The liquid 30 has a refractive index different from that of air. It is possible to monitor the liquid transfer even with a transparent liquid 30 by the difference in the information 40 on the scattered light intensity insofar as the refractive index is different.

For example, the material forming the flow path 10 is COP (cycloolefin polymer) and has a refractive index of about 1.50. The liquid 30 is, for example, blood plasma, and its refractive index can be considered to be equivalent to that of water, so that the refractive index is about 1.33. The refractive index of air is approximately 1.00.

Effect of the Liquid Transfer Monitoring Method of the Present Embodiment

In the liquid transfer monitoring method according to the present embodiment, the light 91 is irradiated on the irregular inner surface 23 of at least one of the first liquid holding portion 21 and the second liquid holding portion 22 to obtain information 40 related to the scattered light intensity. At this time, since the information 40 related to the scattered light intensity varies depending on the presence or absence of the liquid 30 as described above, it is possible to grasp whether the liquid 30 is being transferred to the liquid holding portion 20, and how far the liquid 30 is being transferred based on the obtained information 40 related to the scattered light intensity. In this way the liquid transfer state of the liquid 30 can be monitored even for liquids such as highly transparent samples and reagents that transmit light.

Summary of Sample Measuring Device

A summary of the sample measuring device according to the present embodiment will be described with reference to FIG. 1.

The sample measuring device 100 is a sample measuring device that transfers the liquid 30 to the flow path 10 having at least two liquid holding portions 20 and performs measurement using the liquid 30. The sample measuring device 100 can monitor the transfer of the liquid 30 by executing the liquid transfer monitoring method of the present embodiment.

The sample measurement device 100 includes a liquid transfer unit 110, an illumination unit 120, a photodetection unit 130, a control unit 140, and a measurement unit 145.

The liquid transfer unit 110 applies an external force to the liquid 30 held by the first liquid holding portion 21, and transfers the liquid 30 to the second liquid holding portion 22 connected to the first liquid holding portion 21. The external force applied to the liquid 30 by the liquid transfer unit 110 is, for example, pressure or centrifugal force. The liquid transfer unit 110 includes, for example, a pump, and applies air pressure or water pressure to the liquid 30. The liquid transfer unit 110 includes, for example, a turntable, and rotates an object in which the flow path 10 is formed around a rotation axis. The liquid 30 in the first liquid holding portion 21 is moved toward the second liquid holding portion 22 by the centrifugal force. Also, for example, the liquid transfer unit 110 transfers the liquid 30 to the first liquid holding portion 21 by the centrifugal force. Then, the liquid 30 contained in the first liquid holding portion 21 is transferred to the second liquid holding portion 22 by a capillary phenomenon. Note that the object in which the flow path 10 is formed may be a container that contains the liquid 30, a part of a fluid circuit in the sample measuring device 100, or the like.

The illumination unit 120 irradiates light 91 on the irregular inner surface 23 of at least one of the first liquid holding portion 21 and the second liquid holding portion 22.

The photodetection unit 130 detects the scattered light 92 of the light 91 irradiating the inner surface 23. The photodetection unit 130 outputs a signal according to the detected light amount to the control unit 140.

The control unit 140 acquires the information 40 related to the scattered light intensity based on the signal from the photodetection unit 130, and performs controls to determine the presence or absence of the liquid 30 in the liquid holding portion 20 based on the information 40 related to the scattered light intensity. The control unit 140 is a computer including a processor such as a CPU (Central Processing Unit), an FPGA (field-programmable gate array), and a storage unit such as a ROM (Read Only Memory) and a RAM (Random Access Memory). The control unit 140 executes controls for determining the presence or absence of the liquid 30 by the processor executing a program stored in the storage unit.

The measurement unit 145 is configured to perform a measurement using the liquid 30. The measurement method is not particularly limited. The liquid 30 may be a sample used for measurement or a reagent mixed with the sample. The reagent reacts with the test substance in the sample to cause a directly or indirectly measurable change in the test substance. For example, the reagent emits light depending on the amount of the test substance. Luminescence is, for example, chemiluminescence or fluorescence. The reagent includes, for example, a labeling substance that specifically binds to the test substance. The labeling substance produces a signal that can be measured by the measurement unit 145, for example. According to the measurement item, the presence or absence of the test substance, the amount or concentration of the test substance, and the size and shape of the particulate test substance can be measured by detecting the signal.

The labeling substance includes a chemiluminescent substance or fluorescent substance, radioactive isotope and the like. The reagent also may be one that develops color according to the amount of the test substance, or one that causes turbidity depending on the amount of the test substance. The measurement unit 145 includes a photodetector such as a photomultiplier tube, a photocell, or a photodiode when detecting light emission. The measurement unit 145 includes a radiation detector such as a scintillation counter when detecting radiation. The measurement unit 145 includes a light source and a light receiving element when detecting fluorescence, color, or turbidity.

The control unit 140 may simply determine the presence or absence of the liquid 30 in any of the liquid holding portions 20. The control unit 140 also may be configured to perform controls to monitor the liquid transfer to the second liquid holding portion 22 by determining the presence or absence of the liquid 30 based on the information 40 on the scattered light intensity. In this way, it is possible to monitor whether the liquid transfer from the first liquid holding portion 21 to the second liquid holding portion 22 is properly performed in the sample measurement.

In this case, the control unit 140 transfers the liquid 30 by controlling the liquid transfer unit 110 in step S1 of FIG. 2. In step S2, the control unit 140 causes the illumination unit 120 to irradiate light 91 on the inner surface 23. The photodetection unit 130 detects the scattered light 92. The control unit 140 acquires a signal from the photodetection unit 130. The control unit 140 acquires the information 40 on the scattered light intensity based on the signal acquired from the photodetection unit 130. In step S3, the control unit 140 monitors the liquid transfer to the second liquid holding portion 22 based on the information 40 related to the scattered light intensity. The details of the monitoring of the liquid transfer performed by the control unit 140 are the same as the above-mentioned liquid transfer monitoring method.

Effect of the Sample Measuring Device of the Present Embodiment

In the sample measuring device 100 according to the present invention, since the information 40 regarding the scattered light intensity varies depending on the presence or absence of the liquid 30 in the liquid holding portion 20 similar to the above-described liquid transfer monitoring method, the control unit 140 determines whether the liquid 30 is being transferred to the liquid holding portion 20, and how far the liquid 30 is being transferred based on the acquired information 40 related to the scattered light intensity, and this status can be grasped by a user. In this way the liquid transfer state of the liquid 30 can be monitored even for liquids such as highly transparent samples and reagents that transmit light.

Structural Example of the Photodetection Unit and Illumination Unit

Next, a structural example of the photodetection unit and the illumination unit in the sample measuring device 100 will be described.

In the example shown in FIG. 1, the information 40 related to the scattered light intensity is obtained by the photodetection unit 130 detecting the scattered light 92, and the control unit 140 connected to the photodetection unit 130 analyzing the signal from the photodetection unit 130.

In this way the scattered light 92 generated from the liquid holding portion 22 can be detected, and the information 40 related to the scattered light intensity can be acquired based on the detected signal.

As shown in FIGS. 3 and 4, the light detection unit 130 includes an imaging unit 131 having an image sensor, for example. The control unit 140 (see FIG. 1) acquires and analyzes the captured image of a liquid holding portion 20 as a signal from the light detection unit 130. The analysis performed by the control unit 140 is image analysis. The control unit 140 acquires the information 40 related to the scattered light intensity by image analysis.

In this way the information 40 related to the scattered light intensity can be acquired from the image of the liquid holding portion 20. Unlike the case of detecting the simple light intensity, the distribution of the scattered light intensity corresponding to the position in the liquid holding portion 20 can be analyzed to acquire the information 40 related to the scattered light intensity which is suitable for monitoring the liquid 30.

In FIGS. 3 and 4, the irregular inner surface 23 is the inner bottom surface 24 of the liquid holding portion 20. Here, since the liquid moves along the inner bottom surface 24, the unevenness formed on the inner bottom surface 24 is reliably covered with the liquid 30. Therefore, the difference in the scattered light intensity depending on the presence or absence of the liquid 30 can be grasped with certainty. When a certain amount of volume is ensured in the liquid holding portion 20, the inner bottom surface 24 is the surface having the largest area. Therefore, since the surface that generates the scattered light 92 becomes large, the information 40 related to the scattered light intensity can be acquired more easily.

In the example of FIGS. 3 and 4, in step S2 (see FIG. 2) of obtaining the information 40 related to the scattered light intensity, the inner irregular bottom surface 24 is obliquely irradiated with the light 91 and the scattered light 92 is detected by the imaging unit 131 at a position above the inner bottom surface 24. That is, the illumination unit 120 obliquely irradiates the irregular inner bottom surface 24 with the light 91, and the imaging unit 131 detects the scattered light 92 at a position above the inner bottom surface 24.

In this way the imaging unit 131 can substantially detect just the scattered light 92. Therefore, the information 40 related to the scattered light intensity can be acquired accurately. In the example of FIGS. 3 and 4 as described above, the illumination unit 120 is configured as dark-field illumination for the imaging unit 131.

More specifically, the illumination unit 120 irradiates the light 91 in an oblique direction so that the generated light 91 is not spectrally reflected and is not received by the imaging unit 131. The imaging unit 131 is arranged directly above the inner bottom surface 24 and captures an image facing downward. The irradiation angle 95 of the illumination unit 120 is set so that the reflected optical axis 94 that is spectrally reflected with respect to the outgoing optical axis 93 of the illumination unit 120 passes through the outside of the light receiving part of the imaging unit 131. In this way the spectrally reflected light is not substantially detected by the imaging unit 131, and substantially only the scattered light 92 is detected by the imaging unit 131.

In the examples of FIGS. 3 and 4, the liquid holding portion 20 also is formed so as to extend in the A direction. In this case, it is preferable that the illumination unit 120 is provided so as to emit the light 91 in the direction along the A direction in which the liquid holding portion 20 extends.

Figure 5:
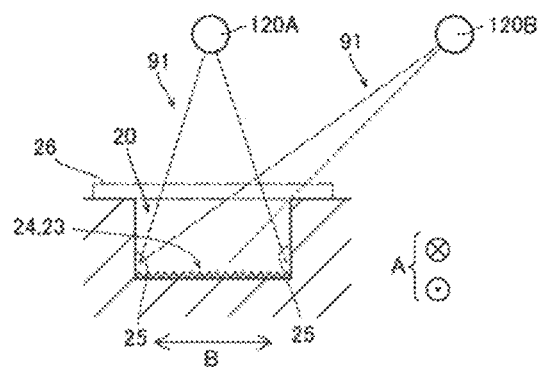
FIG. 5 is a schematic diagram showing a liquid holding portion as viewed from the direction A in FIG. 3.

For example, FIG. 5 is a schematic view of the liquid holding portion 20 of FIG. 3 viewed from the A direction. The illumination unit 120A irradiates the liquid holding portion 20 with light 91 from above the extension line along the A direction to the irregular inner bottom surface 24 of the liquid holding portion 20. The broken line in FIG. 5 indicates the irradiation range of the light 91.

In this case, the scattered light 92 can be generated by irradiating the wide area of the inner bottom surface 24 with the light 91 without causing a shadow due to the inner side surface 25 of the liquid holding portion 20. On the other hand, the illumination unit 120B of FIG. 5 irradiates the inner bottom surface 24 of the liquid holding portion 20 with light from an upper position which is displaced in the B direction orthogonal to the A direction relative to the liquid holding portion 20. In this case, since a part of the light traveling toward the inner bottom surface 24 is blocked by the inner side surface 25 of the liquid holding portion 20, the irradiation range of the light on the inner bottom surface 24 is narrowed. For this reason, it is preferable that the illumination unit 120 is provided so as to emit light in the direction along the direction A in which the liquid holding portion 20 extends.

Note that, in FIG. 5, the liquid holding portion 20 is formed as a space capable of containing a liquid by covering a slot which has the inner bottom surface 24 and the pair of inner side surfaces 25 with the cover member 26 that has a light transmitting property.

Specific Example of Liquid Transfer Monitoring

Next, a specific example of the liquid transfer monitoring method of the present embodiment performed in the sample measuring device 100 will be described.

Figure 6:
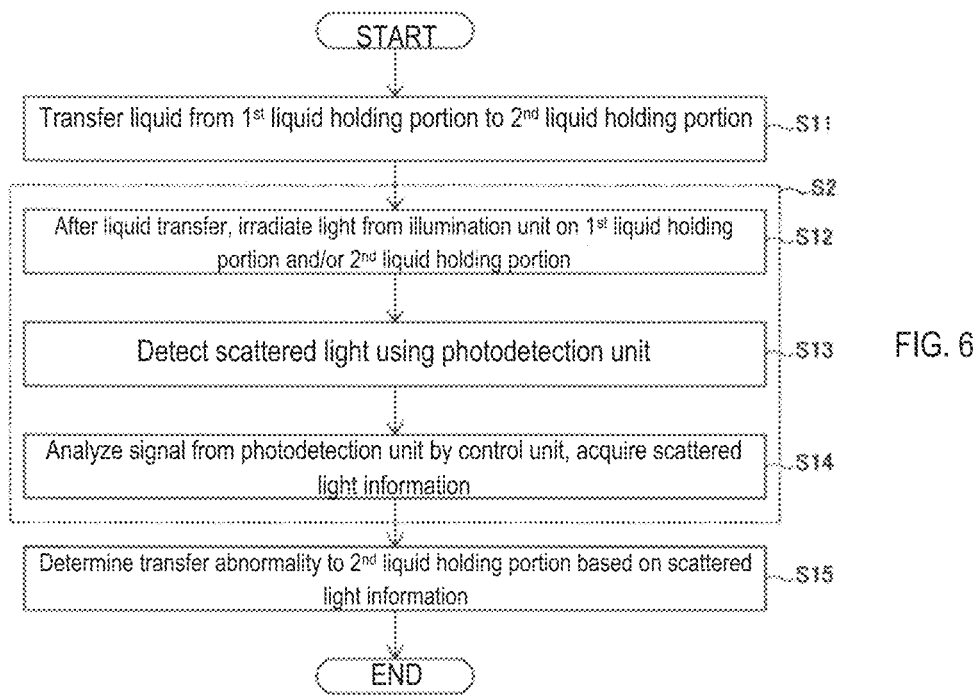
FIG. 6 is a flowchart showing an example of a liquid transfer monitoring method.

As shown in step S11 of FIG. 6, the control unit 140 controls the liquid transfer unit 110 to transfer the liquid 30 in the first liquid holding portion 21 to the second liquid holding portion 22.

The step S2 of acquiring the information 40 relating to the scattered light intensity of FIG. 2 specifically includes steps S12 to S14 of FIG. 6.

In step S12, the control unit 140 causes the illumination unit 120 to irradiate the light 91 on the first liquid holding portion 21 and/or the second liquid holding portion 22. In the example of FIG. 6, in steps S12 to S14 for acquiring the information 40 related to the scattered light intensity, the light 91 is irradiated on the irregular inner surface 23 after the transfer of the liquid 30 is completed.

In this way it is possible to monitor the state of the liquid 30 held in the liquid holding portion 22 after the transfer is completed. Therefore, for example, the amount of the liquid 30 in the liquid holding portion 22 after the transfer is completed, the holding position of the liquid 30, and the like can be confirmed. As a result, it is possible to monitor the quantitativeness of the liquid transfer and improve the accuracy of the liquid transfer process.

In step S13, the control unit 140 causes the light detection unit 130 to detect scattered light. The control unit 140 acquires the detection signal of the scattered light 92 from the light detection unit 130.

In step S14, the control unit 140 acquires the information 40 related to the scattered light intensity. When the scattered light 92 is detected as a captured image, the pixel value of each pixel in the captured image reflects the scattered light intensity. The control unit 140 performs image processing on a region of the captured image in which the inner surface 23 of the first liquid holding portion 21 and/or the second liquid holding portion 22 is imaged to extract information 40 related to the scattered light intensity on the inner surface 23. Note that the relative position of the light detection unit 130 with respect to the inner surface 23 is known, and the coordinates of the inner surface 23 in the captured image are known. Step S2 of FIG. 2 is completed by the steps S12 to S14.

For example, the image analysis is locally performed on a region including at least one of the first liquid holding portion 21 and the second liquid holding portion 22. The control unit 140 extracts only the region including at least one of the first liquid holding portion 21 and the second liquid holding portion 22 from the captured image, and acquires the information 40 related to the scattered light intensity.

By limiting the area in this way, the influence of noise from outside the area can be eliminated. The time required for analysis also can be shortened.

The information 40 related to the scattered light intensity is, for example, the pixel value of the area where the inner surface 23 is imaged. The area where the inner surface 23 is imaged may be composed of a large number of pixels. In that case, the information 40 related to the scattered light intensity may be a representative value of the pixel values of the pixel group included in the region where the inner surface 23 is imaged. The representative value may be, for example, a total value, an average value, a median value, or the like of each pixel value. The information 40 related to the scattered light intensity may be the pixel value of each pixel in the region where the inner surface 23 is imaged. In this case, the information 40 related to the scattered light intensity is numerical information corresponding to the number of pixels in the area where the inner surface 23 is imaged.

In step S15, the control unit 140 determines whether there is a liquid supply abnormality to the second liquid holding portion 22 based on the information 40 related to the scattered light intensity acquired in step S14. That is, when the liquid 30 is transferred from the first liquid holding portion 21 to the second liquid holding portion 22, the control unit 140 determines whether a liquid transfer abnormality has occurred (that is, whether the liquid 30 has been normally transferred). Step S15 corresponds to step S3 of FIG. 2. As described above, the step of monitoring the liquid transfer may include the step of determining whether there is a liquid transfer abnormality.

Steps of Determining the Presence or Absence of Liquid Transfer Abnormality

Figure 7:
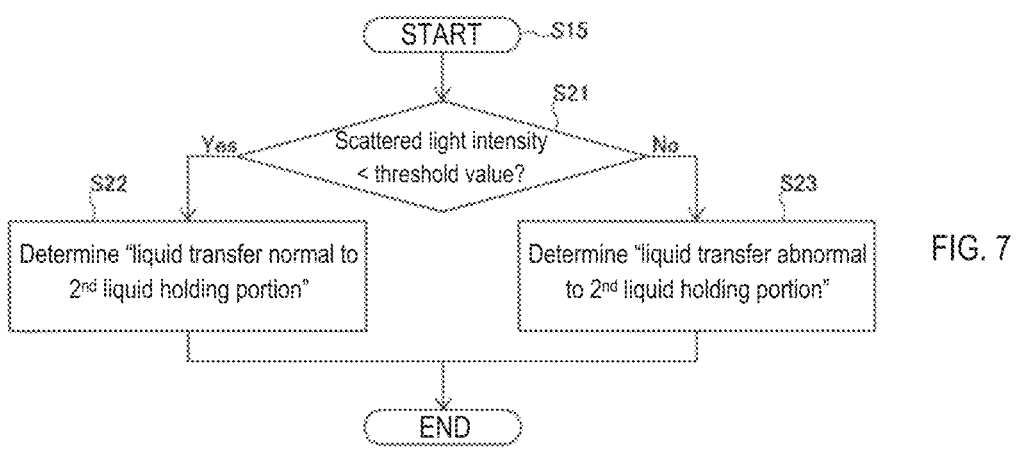
FIG. 7 is a flowchart showing a first example of a method for determining the presence or absence of a liquid transfer abnormality.

FIG. 7 shows an example of steps for determining the presence or absence of liquid transfer abnormality.

In step S21 of FIG. 7, the control unit 140 determines whether the scattered light intensity is less than or equal to a threshold value. When the information 40 related the scattered light intensity is a representative value of the pixel values, the control unit 140 compares the representative value with a threshold value. The threshold value is set at a value between a relatively high level of scattered light intensity when the liquid holding portion 20 is filled with air without the liquid 30 and relatively low level of scattered light intensity when the liquid holding portion 20 filled with the liquid 30.

When the scattered light intensity is less than or equal to a threshold value in step S21, the control unit 140 advances the processing to step S22 and determines that "no liquid transfer abnormality to the second liquid holding portion 22 has occurred". That is, since the detected scattered light intensity corresponds to the scattered light intensity of a relatively low level when the liquid holding portion 20 is filled with the liquid 30, it can be determined that the liquid 30 has been normally transferred to the second liquid holding portion 22.

On the other hand, when the scattered light intensity is neither less than nor equal to the threshold value (the scattered light intensity is higher than the threshold value) in step S21, the control unit 140 advances the process to step S23, and determines the "liquid transfer to the second liquid holding portion 22 is abnormal". That is, since the detected scattered light intensity corresponds to a relatively high level of scattered light intensity when the liquid 30 is not present and the liquid holding portion 20 is filled with air, it can be determined that the liquid 30 has not normally transferred to the second liquid holding portion 22 and there is a region filled with air, or the entire second liquid holding portion 22 remains filled with air.

Figure 8:
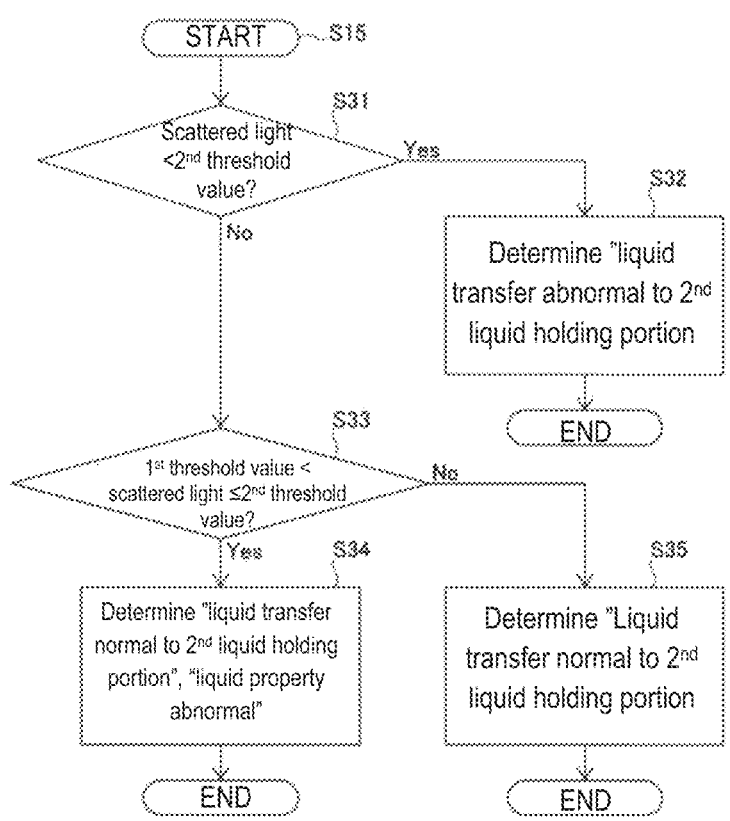
FIG. 8 is a flow chart showing a second example of the method for determining the presence or absence of liquid transfer abnormality.

Another Example of Step for Determining Presence/Absence of Liquid Transfer Abnormality FIG. 8 shows another example of the step of determining the presence/absence of liquid transfer abnormality.

In this example, a property of the liquid 30 to be transferred is determined in addition to the presence/absence of liquid transfer abnormality. At the time of liquid transfer, it is possible that a property of the liquid 30 is different from the assumed state. The difference in a property of the liquid 30 may be that the optical characteristics of the liquid 30, such as turbidity of the liquid 30 and the refractive index thereof, is different from that which is expected. For example, a property of the liquid 30 changes due to an abnormal property of the liquid 30 that is a sample collected from a patient due to a disease or the like, or a chemical change of the liquid 30 due to an external environmental factor. As a specific example of a property abnormality of the liquid 30, if the liquid 30 is plasma, the property abnormality may be chyle, hemolysis, jaundice, and the like.

There may be a difference in the detected scattered light intensity depending on whether the property of the liquid 30 is normal and the property of the liquid 30 is abnormal. For example, when a property of the liquid 30 is abnormal, there may be a scattered light intensity of an intermediate level between the a relatively high level of scattered light intensity when the liquid holding portion 20 is filled with air, and a relatively low level of scattered light intensity when the liquid holding portion 20 is filled with the liquid 30. Therefore, the property of the liquid 30 is determined based on the information 40 related to the scattered light intensity.

In order to identify a liquid transfer abnormality and a property abnormality, the control unit 140 makes a determination based on a first threshold value and a second threshold value. The first threshold is set to a value between a relatively low level of scattered light intensity and an intermediate level of scattered light intensity. The second threshold is set to a value between a relatively high level of scattered light intensity and an intermediate level of scattered light intensity.

In step S31 of FIG. 8, the controller 140 determines whether the scattered light intensity is higher than the second threshold value.

In step S31, when the scattered light intensity is higher than the second threshold value, the control unit 140 advances the process to step S32 and determines that "there is a liquid transfer abnormality to the second liquid holding portion 22". That is, since the detected scattered light intensity corresponds to a relatively high level of scattered light intensity, it can be determined that the liquid transfer is abnormal, as in step S23 of FIG. 7.

On the other hand, when the scattered light intensity is less than or equal to the second threshold value in step S31, the control unit 140 proceeds to step S33 and determines whether the scattered light intensity is higher than the first threshold value.

In step S33, when the scattered light intensity is higher than the first threshold value, the control unit 140 advances the processing to step S34, and determines "there is no abnormality in the liquid transfer to the second liquid holding portion 22 and there is an abnormality in the liquid property. That is, since the detected scattered light intensity corresponds to an intermediate level between the first threshold value and the second threshold value, it can be determined that the property of the liquid 30 is abnormal. Since the scattered light intensity is less than or equal to the second threshold value, it also can be determined that the liquid 30 is normally transferred to the second liquid holding portion 22.

When the scattered light intensity is equal to or lower than the first threshold value in step S33, the control unit 140 advances the process to step S35, and determines "there is no abnormality in the liquid transfer to the second liquid holding portion 22 (the liquid property is also abnormal)". That is, since the detected scattered light intensity corresponds to a relatively low level of scattered light intensity, it is determined that the liquid 30 has been transferred to the second liquid holding portion 22 without abnormality as in step S22 of FIG. 7. Then, since the detected scattered light intensity corresponds to a level lower than the intermediate level, it can be determined that the property of the liquid 30 is normal.

Example of Monitoring the State Before and after Liquid Transfer

Figure 9:
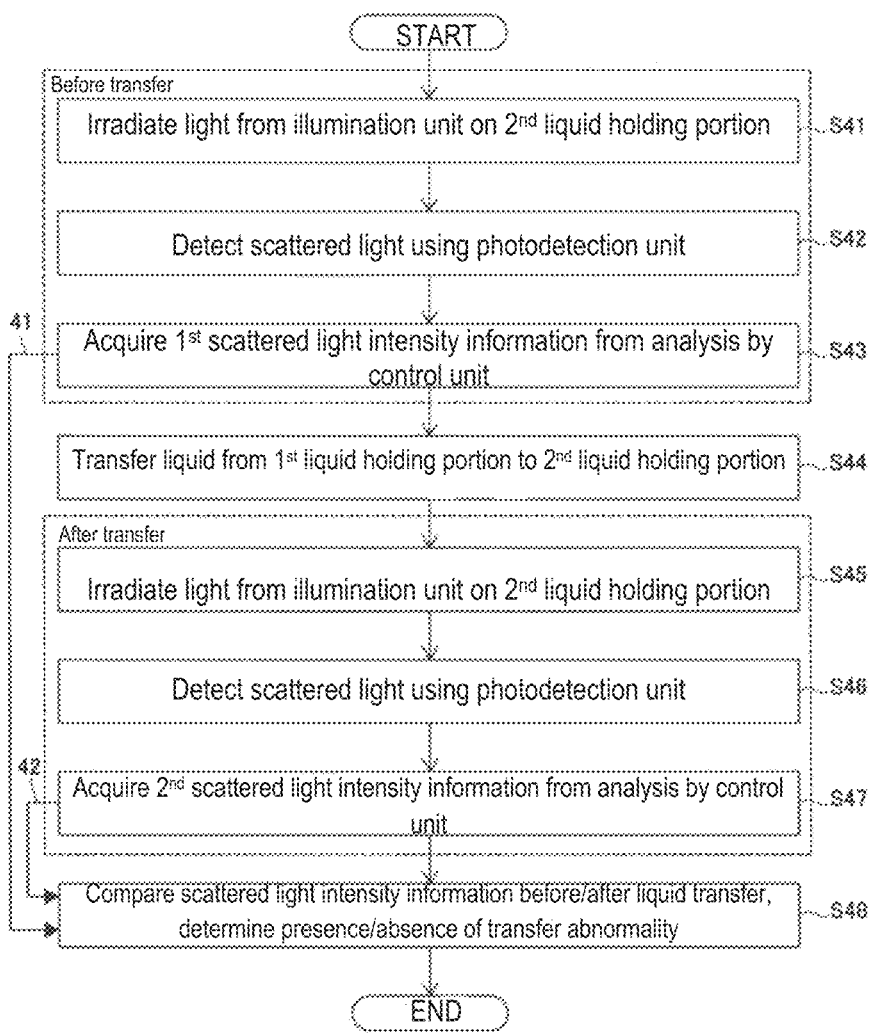
FIG. 9 is a flowchart showing yet another example of the liquid transfer monitoring method.

Next, in the example shown in FIG. 9, steps S43 and S47 for acquiring information related to the scattered light intensity are performed before the liquid 30 is transferred to the second liquid holding portion 22 and after the liquid 30 is transferred.

In this way the information 40 related to the scattered light intensity before and after the transfer of the liquid 30 can be acquired. Therefore, it is possible to evaluate how the state of the second liquid holding portion 22 has changed due to the liquid transfer.

As shown in FIG. 9, in step S41, the control unit 140 controls the illumination unit 120 to cause the light from the illumination unit 120 to irradiate the second liquid holding portion 22 before transfer. In step S42, the control unit 140 causes the light detection unit 130 to detect scattered light. In step S43, the control unit 140 acquires the information 41 related to the first scattered light intensity by analyzing the detected scattered light.

Through these steps S41 to S43, the information 41 related to the first scattered light intensity before transfer is acquired from the second liquid holding portion 22.

In step S44, the control unit 140 controls the liquid transfer unit 110 to transfer the liquid 30 of the first liquid holding portion 21 to the second liquid holding portion 22 by an external force.

In step S45, the control unit 140 controls the illumination unit 120 to cause the light from the illumination unit 120 to irradiate the second liquid holding portion 22 after liquid transfer. In step S46, the control unit 140 causes the light detection unit 130 to detect scattered light. In step S47, the control unit 140 acquires the information 42 related to the second scattered light intensity by analyzing the detected scattered light.

Through these steps S45 to S47, the information 42 related to the second scattered light intensity after liquid transfer is acquired from the second liquid holding portion 22.

In step S48, the control unit 140 determines the presence/absence of an abnormality during the liquid transfer to the second liquid holding portion 22 based on the information 41 on the first scattered light intensity acquired in step S43 and the information 42 on the second scattered light intensity acquired in step S47.

As described above, in the example shown in FIG. 9, the information 40 related to the scattered light intensities acquired before and after the transfer of the liquid 30 are compared to determine whether there is a liquid supply abnormality. The control unit 140 acquires the information 40 related the scattered light intensity before the liquid 30 is transferred to the second liquid holding portion 22 and after the liquid 30 is transferred, and determines the presence/absence if a liquid transfer abnormality by comparing information 40 relating to the scattered light intensities acquired before and after the liquid transfer.

In this way it possible to determine the presence or absence of a liquid transfer abnormality on the basis of the empty state of the second liquid holding portion 22 before the transfer of the liquid 30. Therefore, it is possible to accurately determine the presence or absence of a liquid transfer abnormality.

Figure 10:
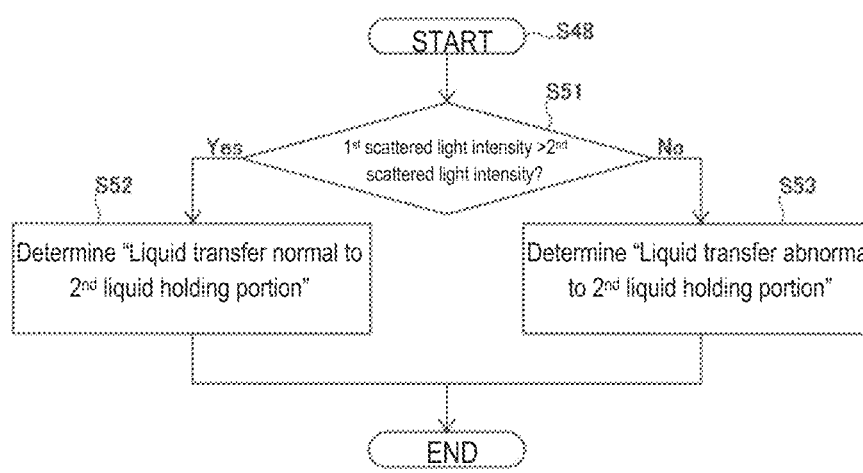
FIG. 10 is a flowchart showing a method for determining presence or absence of a liquid transfer abnormality in FIG. 9.

FIG. 10 shows an example of steps for determining the presence or absence of a liquid transfer abnormality. In step S51 of FIG. 10, the control unit 140 determines whether the first scattered light intensity is higher than the second scattered light intensity.

In step S51, when the first scattered light intensity is higher than the second scattered light intensity, the control unit 140 advances the process to step S52, and determines there is "no abnormality in liquid transfer to the second liquid holding portion 22". That is, since the scattered light intensity detected after the liquid transfer is lower than that before the transfer, the second liquid holding portion 22 is filled with the air before the transfer, and it can be determined that the second liquid holding portion 22 has changed state to being filled with the liquid 30.

On the other hand, when the first scattered light intensity is less than or equal to the second scattered light intensity in step S51, the control unit 140 advances the process to step S53, and determines the "liquid transfer to the second liquid holding portion 22 is abnormal". That is, since the scattered light intensity detected after the liquid transfer is equal to or higher than that before the transfer, the second liquid holding portion 22 is in the state filled with the air before the transfer, it can be determined that the liquid 30 has not been transferred since the state has not changed.

Specific Structural Example of Sample Measuring Device

A specific structural example of the sample measuring device 100 will be described with reference to FIGS. 11 to 15. In the examples shown in FIGS. 11 to 15, the sample measuring device 100 is an immunoassay device that detects a test substance in a sample using an antigen-antibody reaction, and measures the test substance based on the detection result. The detection device 100 is, for example, a compact detection device for PoC (Point of Care) examination, and is configured to be able to execute a measurement operation by a simple operation.

The sample measuring device 100 performs measurement using a cartridge 300 in which the flow path 10 is formed. The cartridge is a replaceable component that has the functions necessary for detecting the test substance contained in the sample. The sample measuring device 100 transfers the liquid 30 in the cartridge 300 as part of the measurement operation. The sample measuring device 100 monitors the liquid transfer of the liquid 30 in the cartridge 300.

The cartridge 300 is a replaceable consumable item. That is, the cartridge 300 is discarded after being used for measurement a preset number of times. The cartridge 300 can be used once or several times. The type of reagent contained in the cartridge 300 differs depending on the measurement item. There may be a plurality of variations of the cartridge 300 for each measurement item. The cartridge 300 also may be capable of measuring a plurality of different measurement items.

Figure 11:
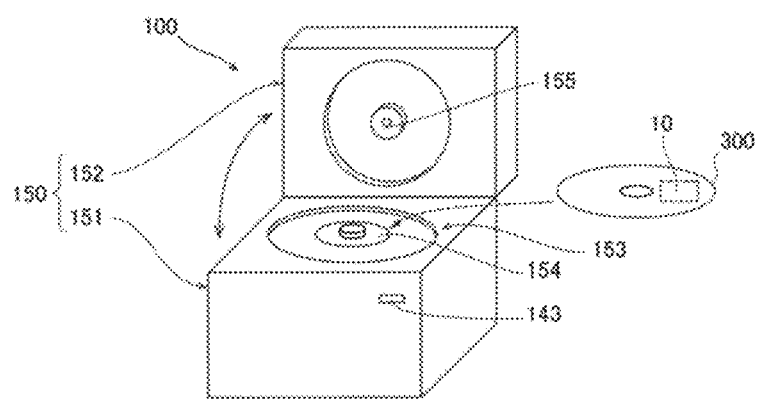
FIG. 11 is a perspective view showing a specific structural example of a sample measuring device.

The cartridge 300 has, for example, a flat plate shape with a space formed inside. FIG. 11 shows an example in which the cartridge 300 is a disk-shaped cartridge having a disc shape. The cartridge 300 includes a plurality of chambers capable of containing the liquid 30. The cartridge 300 includes the flow channel 10 having a plurality of liquid holding portions 20 as shown in FIG. 1. The liquid 30 contained in the liquid holding portion 20 is a sample. The liquid holding portion 20 may store a reagent according to the measurement item of the sample.

Figure 12:
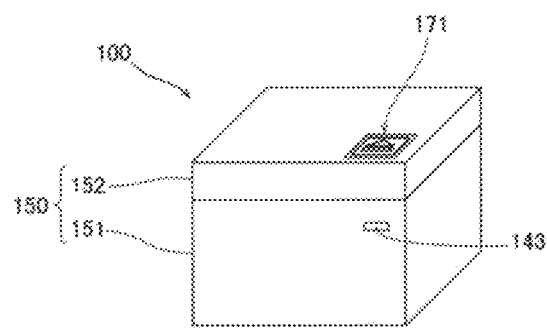
FIG. 12 is a perspective view showing the sample measuring device with a lid closed.

The sample measuring device 100 includes a housing 150 that can accommodate the cartridge 300. The housing 150 includes a main body 151 and a lid 152. The lid 152 is provided so as to cover substantially the entire upper surface of the main body 151. On the upper surface of the main body 151, a placement unit 153 is provided in which the cartridge 300 is placed. The lid 152 is provided so as to be oscillatable relative to the main body part 151 between a state in which the placement unit 153 shown in FIG. 11 is opened, and a state in which the placement unit 153 shown in FIG. 12 is covered.

When the cartridge 300 is set in the placement unit 153 and the lid 152 is closed, the control unit 140 starts the measurement operation. Note that the disk-type cartridge may be installed by a slot loading method in which the cartridge 300 is inserted from an insertion opening formed in the housing 150, or a tray loading method in which the cartridge 300 is placed on a tray that moves inside or outside the housing 150.

Internal Structure of Measuring Device

The internal structure of the sample measuring device 100 will be described with reference to FIG. 13.

A support member 154 that supports the cartridge 300 from below is arranged in the placement unit 153. The support member 154 is composed of, for example, a turntable. The support member 154 is provided on the upper end portion of a rotating shaft 112 of a rotating mechanism 111.

The cover 152 is provided with a clamper 155. The clamper 155 rotatably supports the central portion of the upper surface of the cartridge 300 installed on the support member 154 when the lid 152 is closed. The cartridge 300 is supported by being interposed between the support member 154 and the clamper 155.

Figure 13:
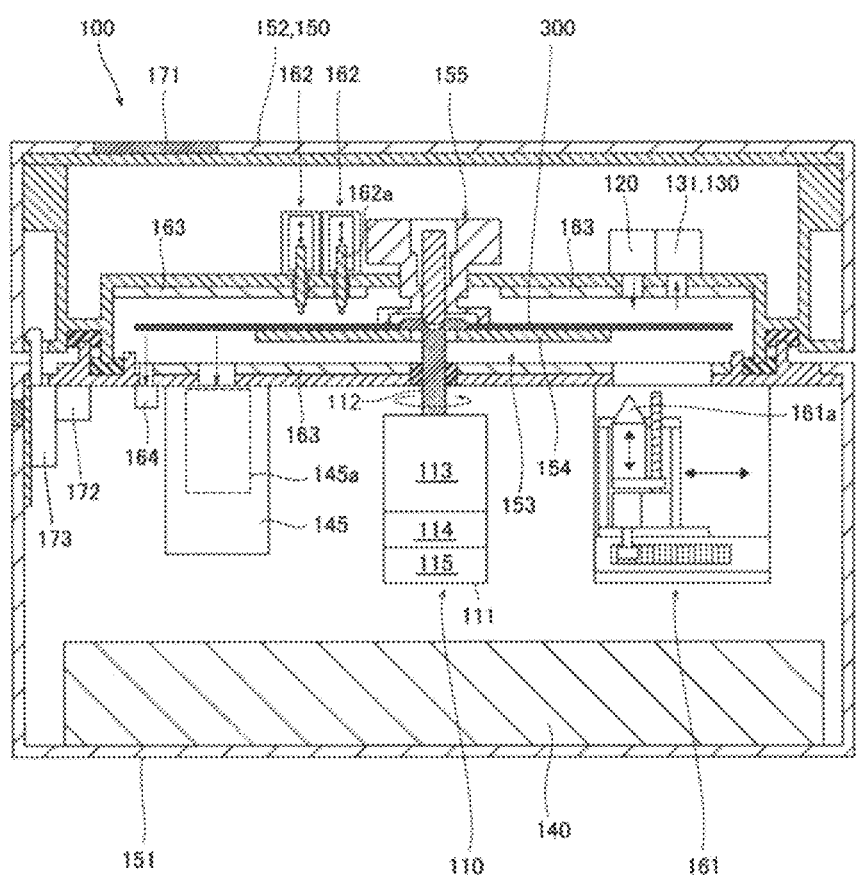
FIG. 13 is a schematic cross-sectional view showing the internal structure of the sample measuring device.

In the example of FIG. 13, the sample measurement device 100 includes a liquid transfer unit 110, an illumination unit 120, a light detection unit 130, a control unit 140, and a measurement unit 145 in a housing 150. The sample measuring device 100 includes a magnet drive unit 161, an opening unit 162, a heater 163, and a temperature sensor 164 in the housing 150.

The liquid transfer unit 110 includes a rotation mechanism 111. The rotating mechanism 111 includes a rotating shaft 112 and a drive unit 113 including a motor. The rotation mechanism 111 drives the drive unit 113 to rotate the cartridge 300 installed on the support member 154 around the rotation shaft 112. The rotation mechanism 111 includes an encoder 114 for detecting the rotation angle of the drive unit 113, and an origin sensor 115 for detecting the origin position of the rotation angle. It is possible to move the cartridge 300 to an arbitrary rotation position by driving the drive unit 113 based on the detection angle of the encoder 114 with the detection position of the origin sensor 115 as a reference.

In the example of FIG. 13, the liquid transfer unit 110 transfers the liquid 30 by rotating the cartridge 300 around the rotation shaft 112. The liquid transfer unit 110 executes at least a part of the measurement process by the rotation mechanism 111. As will be described later as a part of the measurement process, the rotation mechanism 111 rotates to centrifuge the blood sample, transfer the sample, and transfer reagent to the reaction chambers 314 to 319 (see FIG. 16) inside the cartridge 300; the reagent and the sample are stirred, and the magnetic particles are circumferentially transferred between the reaction chambers 314 to 319.

The magnet drive unit 161 includes a magnet 161a and has a function of moving magnetic particles inside the cartridge 300 in the radial direction. The magnet drive unit 161 is arranged below the arrangement unit 153, and is configured to move the magnet 161a in the radial direction. The magnet drive unit 161 also is configured to move the magnet 161a in a direction of approaching or separating from the cartridge 300. By bringing the magnet 161a closer to the cartridge 300, the magnetic particles in the cartridge 300 are magnetized, and by moving the magnet 161a away from the cartridge 300, the magnetism of the magnetic particles is released.

Figure 16:
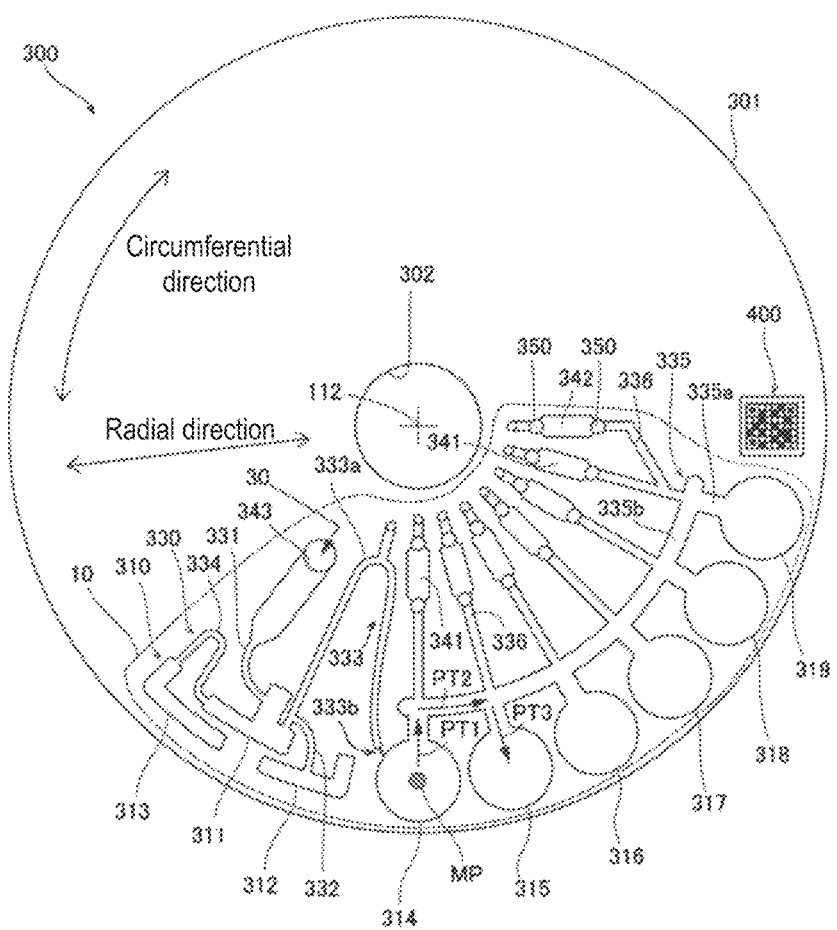
FIG. 16 is a plan view showing a cartridge in which a flow path is formed.

The opening unit 162 projects a pin member 162a that can be advanced and retracted toward the cartridge 300 from above the cartridge 300 arranged in the placement unit 153 so as to abut against the cartridge 300 and press a sealing member 350 inside the cartridge 300 (see FIG. 16). After opening, the opening unit 162 moves the pin member 162a away from the cartridge 300 to the retracted position at which the pin member 162a is in non-contact.

A heater 163 is provided at a position directly below the cartridge 300 arranged in the placement unit 153 and a position immediately above the cartridge 300, respectively. The heater 163 heats the sample contained in the cartridge 300 to a predetermined reaction temperature to accelerate the reaction between the sample and the reagent. The temperature sensor 164 detects the temperature of the cartridge 300 by infrared rays.

The measuring unit 145 includes a light receiving unit at a position facing the cartridge 300 arranged in the placement unit 153 through the opening formed in the main body 151. In this way the measuring unit 145 detects the light generated from the reaction chamber 319 (see FIG. 16) from the light receiving unit. The measurement unit 145 includes a detector 145a that measures the light derived from the test substance moved to the detection position 146 (see FIG. 17). The detector 145a is composed of, for example, a photomultiplier tube, a phototube, a photodiode, or the like. The detector 145a outputs a pulse waveform corresponding to the reception of light particles, that is, photons. The measurement unit 145 includes an internal circuit, counts photons at regular intervals based on the output signal of the detector 145a, and outputs the count value.

The light detection unit 130 includes an imaging unit 131. The imaging unit 131 is provided so as to face the upper surface of the cartridge 300 installed on the support member 154. The imaging unit 131 acquires the image of the cartridge 300. The imaging unit 131 includes, for example, a CCD image sensor, a CMOS image sensor, and the like. The imaging unit 131 acquires, for example, a color image. The imaging unit 131 acquires an image in the form of a still image, for example.

The illumination unit 120 has a light source including, for example, a light emitting diode. The illumination unit 120 generates illumination light when capturing an image. The illumination unit 120 is configured as dark-field illumination for the imaging unit 131.

In the structural example of FIG. 13, the imaging unit 131 and the illumination unit 120 are fixed to the lid 152. The imaging unit 131 directly faces the upper surface of the cartridge 300 via a hole provided in the lid 152. The illumination unit 120 also directly faces the upper surface of the cartridge 300 via a hole provided in the lid 152. Therefore, the imaging range 132 (see FIG. 17) of the imaging unit 131 does not move. Each unit such as the liquid holding portion 20 that is the monitoring target of the cartridge 300 is moved into the imaging range 132 by the rotation of the rotating mechanism 111.

The imaging unit 131 may be movably provided in the housing 150. The imaging unit 131 also may be provided in the main body 151. The position of the imaging unit 131 is not particularly limited insofar as it can image the monitoring target.

In addition, the sample measuring device 100 shown in FIG. 13 includes an operation unit 171 (see FIG. 12) that receives a user operation when opening the lid 152, a detection unit 172 that detects opening and closing of the lid 152, and a lock mechanism 173 that engages with and locks the lid 152. The lid 152 is biased in the opening direction by a force exerting member (not shown). When the lock of the lid 152 in the closed state is released, the lid 152 is opened by the exerted force.

Figure 14:
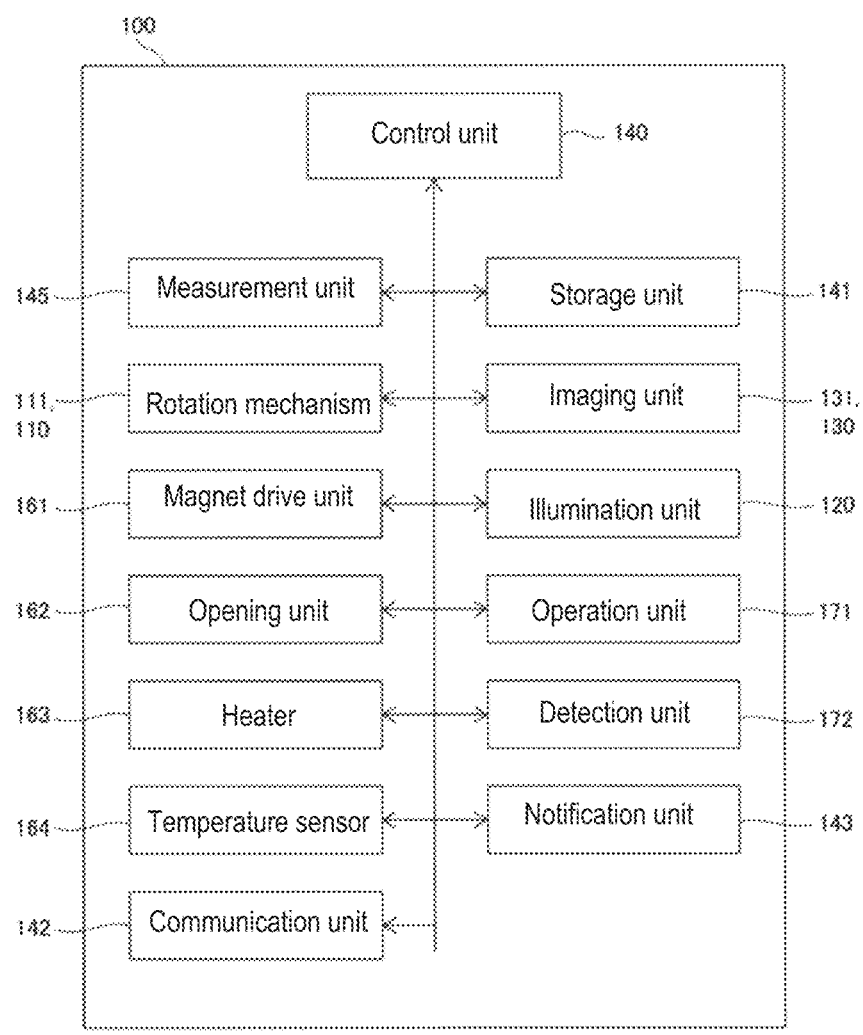
FIG. 14 is a block diagram of the sample measuring device.

FIG. 14 shows a controllable configuration of the sample measuring device 100.

The sample measuring device 100 includes a control unit 140. The control unit 140 includes, for example, a processor and a memory. The processor is composed of, for example, a CPU, an MPU, and the like. The memory is composed of, for example, a ROM and a RAM. The control unit 140 receives a signal from each unit of the sample measuring device 100 and controls each part of the sample measuring unit 100.

The sample measuring device 100 includes a storage unit 141. The storage unit 141 stores at least the image of the monitoring target captured by the imaging unit 131, and the measurement result data 405 (see FIG. 15). The storage unit 141 is composed of, for example, a flash memory, a hard disk, or the like.

The control unit 140 analyzes the captured image. The control unit 140 acquires the information 40 related to the scattered light intensity by performing image analysis on the image of the liquid holding portion 20. The control unit 140 monitors the liquid transfer based on the acquired information 40 on the scattered light intensity. Note that the control unit 140 may individually include a processor for controlling each unit of the sample measuring device 100 and a processor for image processing.

Figure 15:
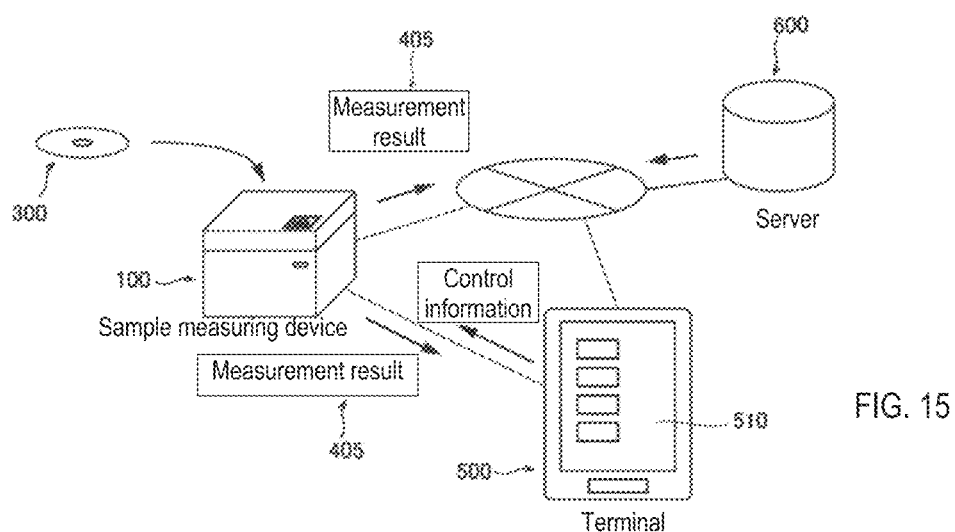
FIG. 15 is a diagram illustrating transmission of measurement result data by a sample measuring device.

The sample measuring device 100 includes a communication unit 142. The communication unit 142 can transmit information to an external device and receive information from the external device. The communication unit 142 includes, for example, a communication module and an interface for external connection. As shown in FIG. 15, the communication unit 142 is capable of performing wired or wireless communication with a terminal 500 capable of communicating with the sample measuring device 100 and with a server 600 via a network. The communication unit 142 may be capable of communicating in multiple types of communication methods. The connection to the network is, for example, a wired LAN or a wireless LAN. The connection with the terminal 500 may be made by a wired LAN, a wireless LAN, Bluetooth (registered trademark), another NFC (near field communication), or the like. The connection with the terminal 500 also may be performed by an interface for external connection such as USB. The server 600 is a server that manages the measurement result data 405.

The control unit 140 can transmit the measurement result data 405 using the cartridge 300 to at least one of the terminal 500 and the server 600 by the communication unit 142. The user can browse the measurement results by accessing the server 600 with any device that can be connected to the network.

The terminal 500 includes, for example, a tablet terminal, a mobile information terminal such as a smartphone, and an information terminal such as a PC (personal computer). The terminal 500 causes the display unit 510 to display the measurement result data 405. The terminal 500 also receives a user operation input via a user interface such as a button displayed on the display unit 510. The input operation is detected by a touch panel on a tablet terminal or a mobile information terminal such as a smartphone, and on a terminal such as a PC via a mouse, a keyboard or other input devices.

The sample measuring device 100 includes a notification unit 143 (see FIG. 11) that notifies of the status of the device. The notification unit 143 notifies of the state of the device by at least one of the color of light, lighting of light, blinking of light, and sound. That is, the notification unit 143 may be an indicator that gives notification by light emission, a speaker or a buzzer that gives notification by sound. Note that the notification of the state of the device can be performed not only in the notification unit 143 but also in a mode in which the display unit 510 of the terminal 500 displays the information through communication via the communication unit 142.

Structural Example of Cartridge

Next, a specific structural example of the cartridge 300 will be described with reference to FIG. 16.

In the example of FIG. 16, the cartridge 300 is a disk-type cartridge including a plate-shaped and disk-shaped substrate 301. Each part in the cartridge 300 is formed by bonding a through hole formed on the substrate 301 and a film (not shown) covering the entire surface including the through hole on both surfaces of the substrate 301 to each other. The film attached to the substrate 301 is formed of a light-transmitting member. The substrate 301 has a thickness such that the temperature of the cartridge 300 can be easily adjusted by the heater 163. For example, the thickness of the substrate 101 is several millimeters, specifically, about 1.2 mm.

A hole 302 and a flow path 10 are formed in the substrate 301. The hole 302 penetrates the substrate 301 at the center of the substrate 301. The cartridge 300 is installed in the sample measuring device 100 so that the center of the hole 302 coincides with the center of the rotating shaft 112. Hereinafter, the radial direction and the circumferential direction of the circle having the hole 302 as the center are referred to as the "radial direction" and the "circumferential direction", respectively.

The flow path 10 includes nine chambers 310, a plurality of passages 330, six storage units 341, one storage unit 342, and an port 343. The liquid 30 is injected into the port 343. The liquid 30 is a blood sample of whole blood collected from a subject. The passage 330 includes passages 331 to 336, and is configured to fluidly connect the plurality of chambers 310, the storage units 341 and 342, and the port 343. Some or all of these passageways 330 and chambers 310 have an inner surface 23 with irregularities. The surface of the substrate 301 other than the flow channel 10 is a smooth surface. The smooth surface here means that the surface roughness is significantly smaller than that of the inner surface 23 having irregularities.

The chamber 310 is a space that can contain a liquid. The nine chambers 310 are arranged in the circumferential direction near the outer periphery of the substrate 301. The plurality of chambers 310 include liquid chambers 311-313 and reaction chambers 314-319.

The liquid chamber 311 receives the supplied liquid 30. The liquid chamber 311 is connected to the port 343 via the passage 331. The blood sample injected from the port 343 is transferred to the liquid chamber 311 via the passage 331 by the centrifugal force generated by the rotation of the cartridge 300.

The liquid chamber 312 receives an excess amount of the liquid 30 that exceeds a certain amount in the liquid chamber 311. The liquid chamber 312 is arranged radially outside the liquid chamber 311 and is connected to the liquid chamber 311 via a passage 332. The liquid 30 flowing into the liquid chamber 311 from the passage 331 is accumulated in order from the radially outer side by the centrifugal force, and the liquid surface position in the radial direction moves inward as the amount of stored liquid increases. When the liquid surface position in the liquid chamber 311 reaches the passage 332, a larger amount of the liquid 30 is moved to the liquid chamber 312 by the action of centrifugal force. Therefore, the amount of the liquid 30 stored in the liquid chamber 311 can be quantified to a constant amount by previously injecting the liquid 30 in an amount exceeding the certain amount.

Note that the liquid component and the solid component contained in the liquid 30 in the liquid chamber 311 are centrifuged by rotating the cartridge 300. The liquid 30 in the liquid chamber 311 is separated into plasma, which is a liquid component, and blood cells and other non-liquid components, which are solid components, by centrifugation. The liquid 30 after the separation process is plasma. The plasma separated in the liquid chamber 311 moves to the passage 333 due to the capillary phenomenon. The width of the passage 333 is narrowed by the connecting portion 333b immediately before the reaction chamber 314, and the plasma fills the inside of the passage 333 until just before the reaction chamber 314.

The passage 333 extends radially inward from the liquid chamber 311, bends at the bent portion 333a, extends radially outward, and is connected to the reaction chamber 314. When the centrifugal force is applied by the rotation while the plasma fills the passage 333, the plasma in the region on the reaction chamber 314 side is transferred to the reaction chamber 314 with the bent portion 333a as a boundary. The volume of the passage 333 from the bent portion 333a to the tip determines a predetermined amount of plasma to be transferred to the reaction chamber 314.

The liquid chamber 313 is provided to prevent the liquid 30 in the liquid chamber 311 after being transferred to the reaction chamber 314 from being transferred to the reaction chamber 314 again. The liquid chamber 313 is arranged radially outside the liquid chamber 311 and is connected to the liquid chamber 311 via a passage 334. When plasma is delivered to reaction chamber 314 via passage 333, passage 334 is also filled with liquid 30. In the passage 334, the liquid 30 is transferred from the liquid chamber 311 to the liquid chamber 313 by the siphon principle until the liquid surface position reaches a balanced position. As a result, the amount of liquid in the liquid chamber 311 decreases, so that once the plasma has been transferred to the reaction chamber 314, the liquid 30 in the liquid chamber 311 is suppressed from being transferred to the reaction chamber 314.

In FIG. 16, six reaction chambers 314, 315, 316, 317, 318, 319 having substantially the same shape are arranged side by side in the circumferential direction so as to be adjacent to each other, and each is connected through a passage 335 extending in the circumferential direction. Among these six reaction chambers 314 to 319, the test substance is sequentially transferred one by one from the one side (reaction chamber 314 side) to the other side (reaction chamber 319 side) via the passage 330.

Reagents stored in the corresponding storage units 341 are transferred to the reaction chambers 314 to 319 via the passages 336. The liquid 30 containing the test substance also is transferred to the reaction chamber 314 via the passage 333. The liquid 30 containing the test substance is plasma centrifuged from whole blood. Magnetic particles MP are enclosed in the reaction chamber 314. In the reaction chamber 314, the test substance contained in the liquid 30 is made into a complex with the magnetic particles MP. Therefore, after the reaction chamber 314, the test substance bound to the magnetic particles MP is transferred to the passage 335 and the other chamber 310 by the combination of the rotation of the cartridge 300 and the action of the magnetic force.

The passage 335 includes six radial regions 335a extending in the radial direction and one arc-shaped circumferential region 335b extending in the circumferential direction. The circumferential region 335b is connected to the six radial regions 335a. The six radial regions 335a are connected to the reaction chambers 314 to 319, respectively. The six storage units 341 are connected to the passage 335 via a passage 336 in the radial direction. The six storage units 341 are arranged side by side in the radial direction with the corresponding reaction chambers 314 to 319. The housing 342 is connected to the reaction chamber 319 mainly via a passage 336 extending in the radial direction. A total of seven storage units 341 and 342 are arranged on the inner peripheral side of the cartridge 300, and a total of six reaction chambers 314 to 319 are arranged on the outer peripheral side of the cartridge 300.

Each of the receiving unit 341 and the receiving unit 342 accommodates a reagent, and includes a sealing body 350 on the upper surface on the inner side in the radial direction. The sealing body 350 is configured to be opened by being pressed from above by the opening unit 162 (see FIG. 13) of the sample measuring device 100. Before the sealing body 350 is opened, the reagent in the container 341 does not flow into the passage 336. When the sealing body 350 is opened, the reagent in the container 341 can flow into the passage 336. When the cartridge 300 is rotated after the stopper is opened, the reagent moves to the corresponding reaction chambers 314 to 319 by the centrifugal force.

Note that the storage unit 341 and the storage unit 342 each accommodate a reagent that can be measured once. That is, the cartridge 300 is a one-time-use measurement cartridge capable of performing one-time measurement on the test substance.

The measurement process includes a process of stirring the test substance and the reagent in the chamber by rotating the cartridge 300. That is, the rotation speed of the cartridge 300 is changed, and acceleration and deceleration are alternately repeated. By the acceleration/deceleration, the liquid is moved back and forth in the chamber 310 in the circumferential direction, and the complex is dispersed in the reagent.

In the sample measuring device 100, the test substance and the labeling substance are carried on the magnetic particles MP in the chamber 310, and the magnetic particles MP are sequentially transferred to a plurality of chambers, so that the reagent and the test substance are stirred in the respective reaction chambers 314 to 319. Finally, the magnetic particles carrying the test substance and the labeling substance are moved to the reaction chamber 319, and the labeling substance is detected by the sample measuring device 100, whereby the measurement is performed.

Note that the flow channel 10 in the example of FIG. 16 is formed only in a region of approximately one third of the substrate 301. However, the present invention is not limited to this, and two more channels 10 may be formed in the remaining two-thirds region of the substrate 301, and three channels 10 may be provided in the substrate 301. Note that one flow path 10 may be formed over a region larger than a one-third region of the substrate 301.

When a plurality of flow channels 10 are provided, the measurement process of the same measurement item may be performed in each flow channel 10, or the measurement process of different measurement items may be performed.

The numbers and shapes of the chambers 310 and the passages 330 also are not limited to those shown in FIG. 16. The configuration of each part of the flow channel 10 is determined according to the content of the sample processing assay performed in the flow channel 10.

In the structural example of FIG. 16, the cartridge 400 is provided with the identifier 400. The identifier 400 is an information recording medium from which information can be read by imaging. In FIG. 16, the identifier 400 is a two-dimensional code. The identifier 400 is provided on the cartridge 300 by attaching a label on which a two-dimensional code is printed or by directly printing the two-dimensional code on the surface of the cartridge 300. The identifier 400 also may be a barcode.

The control unit 140 reads the information recorded in the identifier 400 by acquiring the image of the identifier 400 with the imaging unit 131. The control unit 140 controls the measurement operation based on the read information. The identifier 400 includes at least one of information for specifying a measurement item that can be measured using the cartridge 300, information about a reagent contained in the cartridge 300, and identification information for specifying the cartridge 300.

Imaging of Monitoring Target

Figure 17:
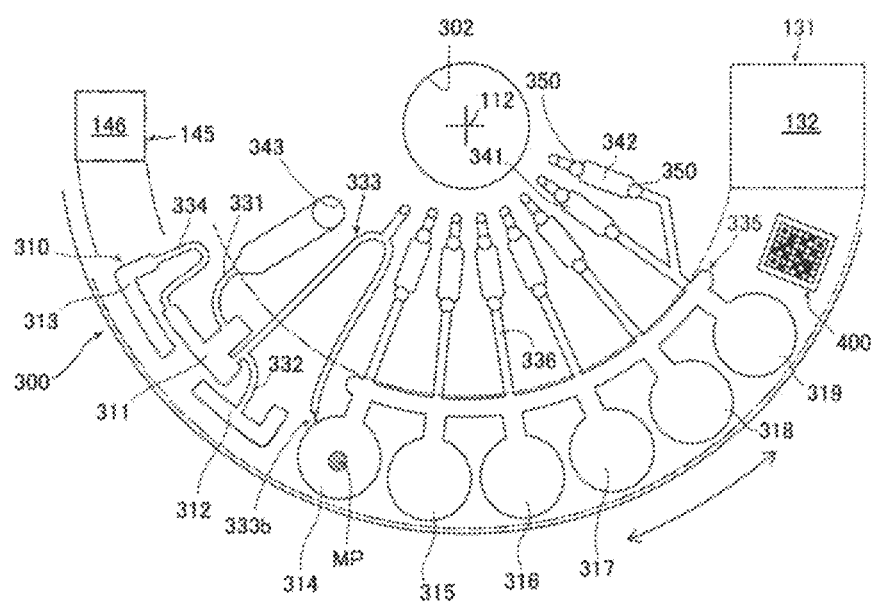
FIG. 17 is a diagram showing a positional relationship between each unit of the cartridge and the imaging unit and the measurement unit.

As shown in FIG. 17, the imaging range 132 of the imaging unit 131 is arranged on the circumferential movement path of the monitoring target due to the rotation of the cartridge 300.

In the structural example of FIG. 17, nine chambers 310 can be moved to the imaging range 132. The imaging unit 131 can individually image each of the nine chambers 310. A part or all of the passage 330 can be moved to the imaging range 132. The imaging unit 131 can divide and image the passage 330 connected to the reaction chambers 314 to 319. For example, the connection portion 333b between the passage 333 and the reaction chamber 314 can be moved to the imaging range 132. The imaging unit 131 can image the connection portion 333b between the passage 333 and the reaction chamber 314. That is, each of the nine chambers 310 and each passage 330 can be monitored. The monitoring target may be any one of these units, a plurality thereof, or all.

Note that the identifier 400 can be moved to the imaging range 132 in addition to the monitoring target. The identifier 400 is provided in advance at a predetermined position in the circumferential direction of the cartridge 300 so as to have a predetermined positional relationship with the flow path 10. That is, the relative rotation angle of each monitoring target is set in advance with reference to the reading position of the identifier 400. The control unit 140 controls the rotation position of the cartridge 300 based on the reading position and the relative rotation angle between each unit of the cartridge 300 and the reading position with the origin position detected by the origin sensor 115 as a reference. The identifier 400 not only records information, but also functions as a rotational position reference.

Specific Example of Liquid Transfer Monitoring

Next, a specific example of liquid transfer monitoring in the structural example shown in FIGS. 11 to 17 will be described.

When transferring the liquid 30 in one of the chambers 310 or passages 330 of the cartridge 300 to another chamber or passage, the control unit 140 sets the chamber or passage serving as the transfer source as the first liquid holding portion 21, and the chamber or passage that is the transfer destination is the second liquid holding portion 22. Then, the control unit 140 monitors the liquid transfer from the first liquid holding portion 21 to the second liquid holding portion 22.

As an example of the monitoring target, here, the monitoring of liquid transfer from the liquid chamber 311 to the passage 333 shown in FIG. 16 will be described. That is, an example in which the liquid chamber 311 is the first liquid holding portion 21 and the passage 333 is the second liquid holding portion 22 will be described. The passage 333 has an inner bottom surface 24 having irregularities. The liquid 30 transferred to the passage 333 is transparent plasma.

Liquid Transfer Abnormality

Figure 18:
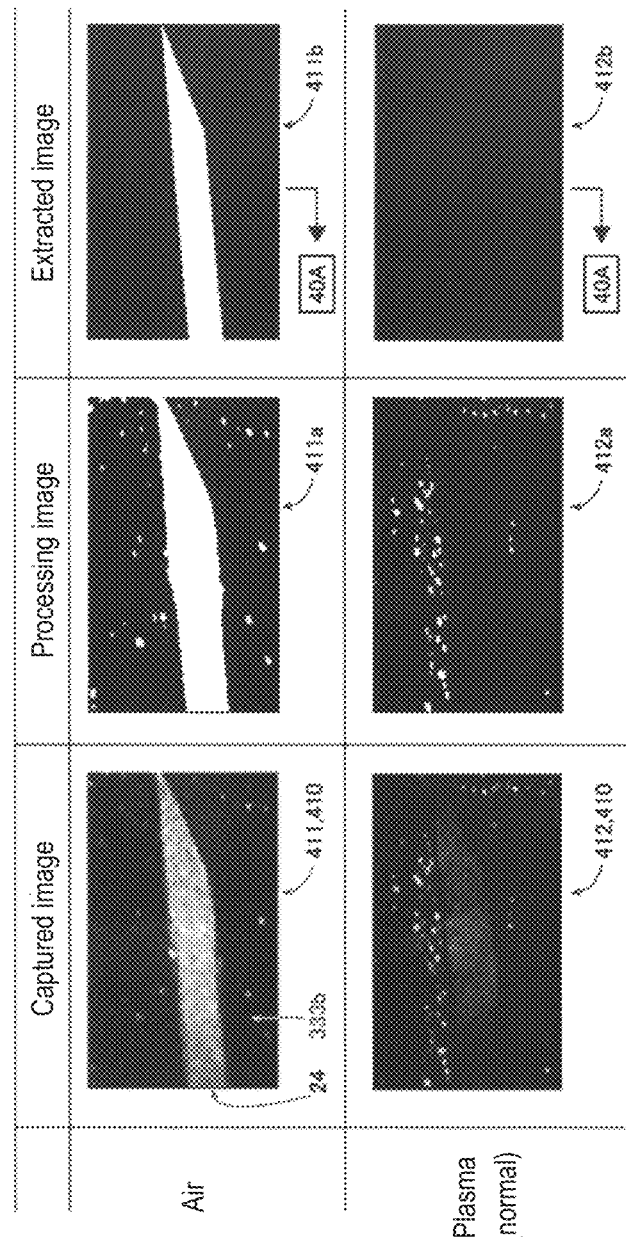
FIG. 18 is a diagram showing a captured image of a connection part acquired in liquid transfer monitoring.

FIG. 18 shows an image 410 of the connection portion 333b between the passage 333 and the reaction chamber 314. As described above, the volume of the blood plasma to be transferred to the reaction chamber 314 is quantified by the volume from the bent portion 333a of the passage 333 to the connection portion 333b. Therefore, in the passage 333, when the liquid 30 is filled up to the connection portion 333b, it can be confirmed that the liquid transfer is normally performed. The liquid transfer abnormality occurs when the air existing in the passage 333 before the liquid transfer remains due to the formation of an air region not filled with the liquid 30 in the connection portion 333b. Therefore, the control unit 140 determines the presence or absence of a liquid transfer abnormality by analyzing the presence or absence of an air region in which the liquid 30 does not exist in the image 410 of the connection portion 333b.

Specifically, since the scattered light 92 (see FIG. 3) from the irregular inner bottom surface 24 is detected in the image 411 of the connection portion 333b in a state filled with air before liquid transfer, the pixel value becomes high level over substantially the entire inner bottom surface 24. Note that due to the dark field illumination (see FIGS. 3 and 4), spectrally reflected light from a portion of the cartridge 300 other than the inner bottom surface 24 having no irregularity is scarcely detected. Therefore, the image 411 is captured essentially as an image in which only a portion in which scattered light is generated.

In the image 412 of the connection portion 333b that is filled with the liquid 30 after the liquid has been transferred, light scattering is suppressed, so that the pixel value becomes a low level in almost the entire inner bottom surface 24. In the example of FIG. 18, the dark field illumination also suppresses the pixel value of the inner bottom surface 24 to a level equivalent to the background in the image.

The control unit 140 performs image analysis to acquire the information 40A related to the scattered light intensity.

The image analysis includes a binarization process that divides the image into a region in which the scattered light intensity is smaller than a binarization threshold and a region in which the scattered light intensity is equal to or larger than the binarization threshold. In this way noise in the image can be removed, so that image analysis can be performed accurately.

The binarization threshold is a value between the distribution range of pixel values detected on the inner bottom surface 24 of the image 411 and the distribution range of pixel values detected on the inner bottom surface 24 of the image 412. For example, assuming that the pixel value is represented by 256 gradations, in the binarization process the value of a pixel having a pixel value smaller than the binarization threshold value among the images 411 and 412 becomes the lower limit value (=0, black); that is, the value of a pixel having a pixel value equal to or greater than the binarization threshold becomes the upper limit value (=255, white).

FIG. 18 shows a processed image 411a after the binarization process on the image 411, and a processed image 412a after the binarization process on the image 412. In the image 411, the entire inner bottom surface 24 in which scattered light is detected is equal to or greater than the binarization threshold, and therefore the pixel value of the inner bottom surface 24 in the processed image 411a becomes the upper limit value (255, white). In the image 412, the pixel value of the inner bottom surface 24 where the scattered light is detected has a pixel value smaller than the binarization threshold, so that the pixel value of the inner bottom surface 24 in the processed image 412a is the lower limit value (black).

The information 40A related to the scattered light intensity is the area information of the region where the scattered light intensity is equal to or higher than the binarization threshold value, which is obtained by the binarization process. In this way it is possible to monitor for liquid transfer abnormality based on the area of the region where the scattered light 92 is detected. That is, the size of the region where the liquid 30 is present and the size of the region where the liquid 30 is not present and air exists can be quantitatively grasped.

Specifically, first, the control unit 140 extracts a region in which the connection portion 333b appears from the processed image 411a and the processed image 412a, and removes the background region other than the connection portion 333b. The area where the connection portion 333b appears in the image is known from the design information. Then, the control unit 140 obtains the number of pixels having the high pixel value (255) included in the extraction regions of the processed image 411a and the processed image 412a. The calculated number of pixels represents the area of the region where the scattered light intensity is equal to or higher than the binarization threshold.

FIG. 18 shows an extracted image 411b after the region extraction processing for the processed image 411a, and an extracted image 412b after the extraction processing for the processed image 412a. In the example of FIG. 18, the area value in the extracted image 411b is "5558", which corresponds to the area of almost the entire connection portion 333b. On the other hand, the area value in the extracted image 412b is "0".

In the present embodiment, in the step of monitoring the liquid 30, the control unit 140 compares the area value of the region where the scattered light intensity is equal to or higher than the binarization threshold value with the area threshold value, and based on the comparison result, determines whether there is a liquid transfer abnormality to the liquid holding portion 22. The area threshold is set to a value between the area value in the extracted image 411b and the area value in the extracted image 412b.

In this way it is possible to determine the presence or absence of a liquid transfer abnormality by comparing the area value of the region where the scattered light 92 is detected with the area threshold value. That is, the presence or absence of a liquid transfer abnormality can be determined from the magnitude relationship between the area value and the area threshold value of the region in which the liquid 30 does not exist and air exists.

When the area value acquired as the information 40A regarding the scattered light intensity is equal to or less than the area threshold value, the control unit 140 determines that "no liquid transfer abnormality" has occurred. When the area value is larger than the area threshold value, the control unit 140 determines that there is a liquid transfer abnormality.

Note that, in FIG. 18, for convenience, a state in which the entire connection portion 333b is filled with air and a state after normal liquid transfer in which the entire connection portion 333b is filled with the liquid 30 are compared and described; however, the circumstance in which the liquid transfer abnormality occurs is most likely is when a part of the connection portion 333b is filled with the liquid 30, and a region partially filled with air is formed at the tip portion. For example, in the image 410 of FIG. 18, about half is filled with air from the tapered tip side.

Therefore, in reality, the area value in the case of the liquid transfer abnormality is lower than the above-mentioned "5558". The area threshold value is set to a predetermined value close to "0", which is the area value when the liquid is normally sent, in consideration of the actually permissible quantitative error tolerance range. Note that the area value (the number of pixels) shown here is merely an example. It is important that there is a significant difference between the area value when the solution is normally transferred and the area value when the solution is abnormally transferred.

Liquid Abnormality Determination

Next, the determination of the presence/absence of abnormality of the liquid 30 will be described.

The control unit 140 determines whether a property of the liquid 30 transferred to the second liquid holding portion 22 is normal. In the example shown in FIG. 19, the liquid 30 is plasma and the abnormality of the liquid 30 is chyle. In this way it is possible to determine whether the milky plasma is cloudy due to high lipid content in the blood. In this way it is possible to monitor the presence or absence of abnormality of the sample that affects the measurement.

Plasma is usually a yellowish, transparent liquid. Milky plasma is cloudy plasma due to its high lipid content in blood. That is, lipids in plasma are bound to proteins to form spherical particles, and the spherical particles are dispersed in plasma to be suspended as a white color. Milky plasma becomes a factor that degrades the measurement accuracy in the immunoassay.

Figure 19:
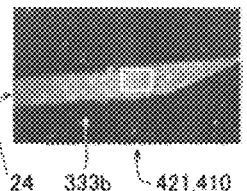
FIG. 19 is a diagram showing a captured image of a connection part illustrating a method of determining abnormality of a sample.

FIG. 19 shows an image 421 of the connection portion 333b filled with air, and an image 422 of the connection portion 333b filled with milky plasma. Since chyle in plasma can be said to be a suspension of spherical particles, light is multiply scattered by the spherical particles in chyle plasma to generate scattered light 92. In this way, in the state filled with milky plasma, the scattered light intensity may reach a high level as in the state filled with air.

Therefore, the control unit 140 acquires the information 40B regarding the scattered light intensity for determining the presence or absence of abnormality of the liquid 30 by image analysis.

Specifically, the image analysis includes a process of calculating an index value indicating dispersion in scattered light intensity in the area where the scattered light 92 is detected. The control unit 140 calculates an index value indicating the dispersion of scattered light intensity in the region where the scattered light 92 is detected.

Enlarged images 421a and 422a in FIG. 19 are enlarged images of the rectangular areas shown in images 421 and 422, respectively. As can be seen by comparing the magnified images 421a and 422a, the scattered light intensity varies between the magnified image 421a filled with air and the magnified image 422a filled with chyle plasma.

That is, in the liquid holding portion 20 filled with air, only the irregular inner bottom surface 24 scatters light, so the scattered light intensity varies depending on the unevenness of the inner bottom surface 24. In contrast, in the liquid holding portion 20 filled with milky plasma, the scattered spherical particles cause multiple scattering in the whole milky blood plasma, so that the scattered light intensity becomes uniform. As a result, the scattered light intensity becomes substantially uniform in the entire liquid holding portion 20. That is, the scattered light intensity dispersion in the enlarged image 422a is significantly less than that in the enlarged image 421a.

The process of calculating the index value indicating the dispersion in the scattered light intensity is, for example, the Sobel filter process. The Sobel filter calculates the non-uniformity of the pixel values of the neighboring pixels as the pixel value of the center pixel using the pixel values of the neighboring pixels centered on the center pixel. According to the Sobel filter, a pixel value in a region in the image where the variation in pixel value is large becomes relatively high in the pixel value by the filtering process. In the area in which the dispersion in pixel value in the image is small, the pixel value becomes a relatively low level by the filtering process. Therefore, the pixel value of each pixel in the processed image after the Sobel filter process does not indicate the scattered light intensity but serves as an index value indicating the magnitude of the scattered light intensity dispersion.

FIG. 19 shows processed images 421b and 422b after the Sobel filter processing on the enlarged images 421a and 422a. In the enlarged image 421a, the scattered light intensity has a large dispersion, and thus in the processed image 421b after the filter processing, regions having a high pixel value (white regions) are distributed over the entire region. On the other hand, in the enlarged image 422a, since the scattered light intensity has a small variation, in the processed image 422b after the filter processing, there is only a region with a low pixel value (black region), and there is no region with a high pixel value (white region). In this way the degree of dispersion in scattered light intensity can be evaluated from the processed image.

The information 40B related to the scattered light intensity is the sum of the index values in the image. In this way it is possible to evaluate the degree of dispersion in scattered light intensity. It is possible to objectively evaluate whether the detected scattered light 92 is generated from the irregular inner surface 23 based on the degree of dispersion in the scattered light intensity.

Specifically, the control unit 140 extracts the region in which the connection portion 333b appears from the processed image 421b and the processed image 422b by the Sobel filter, and removes the background region other than the connection portion 333b. Then, the control unit 140 obtains the sum of pixel values included in the extraction regions of the processed image 421b and the processed image 422b. In the example of FIG. 19, the sum of the pixel values of the image 421 after the filter processing is "63593", and the sum of the pixel values of the image 422 after the filter processing is "3726". The total sum of the pixel values included in the extraction region corresponds to the area of the region (white region of the processed image) in which the scattered light intensity has a large dispersion in the extraction region.

In the step of monitoring the liquid 30, the control unit 140 compares the sum of the index values with the threshold value of the sum, and based on the comparison result, determines the presence or absence of abnormality of the liquid 30 sent to the second liquid holding portion 22. The threshold value of the sum of the index values is set to a value between the sum in the processed image 421b and the sum in the processed image 422b.

In this way it is possible to determine whether there is an abnormality in the liquid 30 itself in addition to whether there is an abnormality in the liquid transfer of the liquid 30. That is, it can be determined from the index value of the scattered light intensity dispersion whether the detected scattered light 92 is generated from the irregular inner surface 23 or multiple scattering in the liquid 30. Therefore, it is possible to determine whether an abnormal component causing multiple scattering is contained in the liquid 30.

The control unit 140 determines that "there is a liquid abnormality" when the total sum of the index values acquired as the information 40B related to the scattered light intensity is equal to or less than the threshold value. When the total sum of the index values is larger than the threshold value, the control unit 140 determines that "there is no abnormality in the liquid".

The control unit 140 combines the information 40A and 40B related to the scattered light intensity to monitor the liquid transfer. Based on the information 40A related to the scattered light intensity and the information 40B related to the scattered light intensity, the control unit 140 determines (1) "no liquid transfer abnormality, no liquid abnormality", or (2) "no liquid transfer abnormality, liquid abnormality", or (3) "abnormal transfer".

In the above description, an example of liquid transfer monitoring in the connection portion 333b of the passage 333 has been shown, but the monitoring target is not limited to this.

The above-described analysis method of the image 410 is merely an example. The image analysis may be performed by any method and criteria. For example, a Prewitt filter may be used instead of the Sobel filter in the process of calculating the index value indicating the dispersion in the scattered light intensity. The index value of the scattered light intensity dispersion may be the variance or standard deviation of the pixel values in the image. Instead of the area value, the sum of the pixel values may be acquired as the information 40A regarding the scattered light intensity. As the information 40B regarding the scattered light intensity, the number of pixels having an index value equal to or larger than the threshold value (that is, the area value) may be acquired instead of the total sum of the index values.

Description of Operation of Sample Measuring Device

Next, the operation of the sample measuring device 100 will be described with reference to FIG. 20. In the following description, FIG. 13 will be referred to for the structure of the sample measuring device 100. The structure of the cartridge 300 will be described with reference to FIG. 16 and FIG. 17.

First, as a preparation operation, the user injects the blood sample collected from the subject from the port 343 of the cartridge 300. The user injects a larger amount of sample than the predetermined amount that can be stored in the liquid chamber 311 from the injection port 343. As an example of measurement items of the cartridge 300, a measurement example of hepatitis B surface antigen (HBsAg) is shown. The test substance in the blood sample contains an antigen. As such, the antigen is hepatitis B surface antigen (HBsAg). The test substance may be one or more of an antigen, an antibody, or a protein. The measurement item may be prostate specific antigen (PSA), thyroid stimulating hormone (TSH), thyroid hormone (FT4), or the like.

Predetermined reagents are stored in advance in the storage units 341 and 342 of the cartridge 300 and the reaction chamber 314. Specifically, the R1 reagent is stored in the storage unit 341 located in the radial direction of the reaction chamber 314. The reaction chamber 314 contains the R2 reagent. The R3 reagent is stored in the storage unit 341 located in the radial direction of the reaction chamber 315. A cleaning liquid is stored in the storage unit 341 located in the radial direction of the reaction chambers 316 to 318. An R4 reagent is stored in the storage unit 341 located in the radial direction of the reaction chamber 319. The container 342 contains the R5 reagent.

Figure 20:
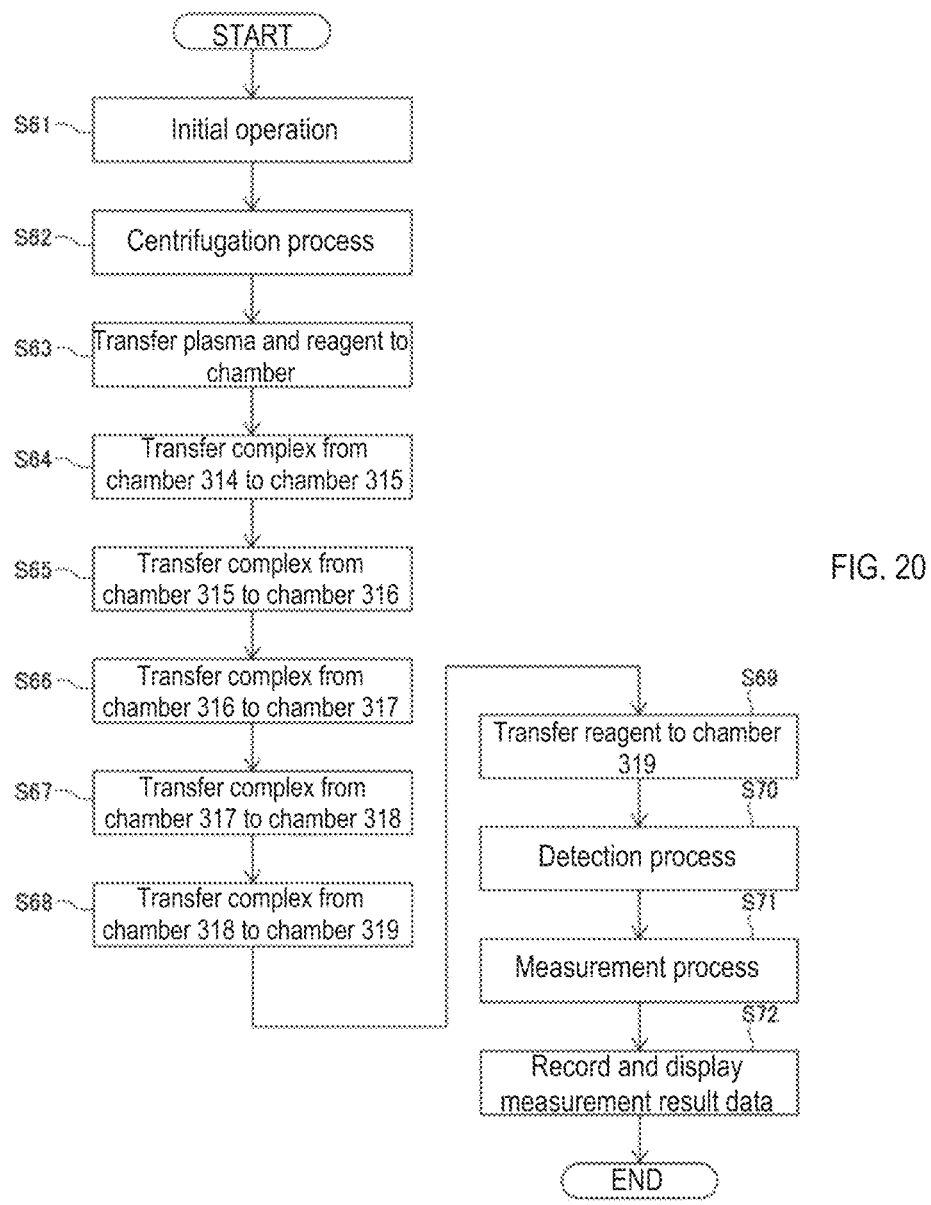
FIG. 20 is a flowchart showing the measurement operation of the sample measuring device.

In step S61 of FIG. 20, the control unit 140 executes an initial operation for starting measurement.

Specifically, control unit 140 determines whether lid 152 is closed. When the lid 152 is closed, the controller 140 causes the reading operation of the identifier 400. The control unit 140 causes the rotation mechanism 111 to rotate the cartridge 300 so that the identifier 400 is arranged within the imaging range 132 of the imaging unit 131. The control unit 140 causes the illumination unit 120 and the imaging unit 131 to photograph the two-dimensional code that is the identifier 400. The control unit 140 acquires the information recorded in the identifier 400 from the captured image. The control unit 140 also acquires the rotational position of each monitoring target based on the origin position detected by the origin sensor 115 and the reading position of the identifier 400.

The control unit 140 starts the measurement processing by the sample measuring device 100 after step S62. In each step, when a part of the measurement process is executed in any of the monitoring targets, the control unit 140 positions the monitoring target in the imaging range 132 of the imaging unit 131 by the rotation mechanism 111, and the imaging unit 131 and captures an image. The control unit 140 monitors whether the measurement process is normally executed based on the captured image of the imaging unit 131.

In step S62, the control unit 140 performs a process of centrifuging the liquid 30 that is the sample and a process of transferring the liquid 30 after centrifugation to the passage 333.

Figure 21:
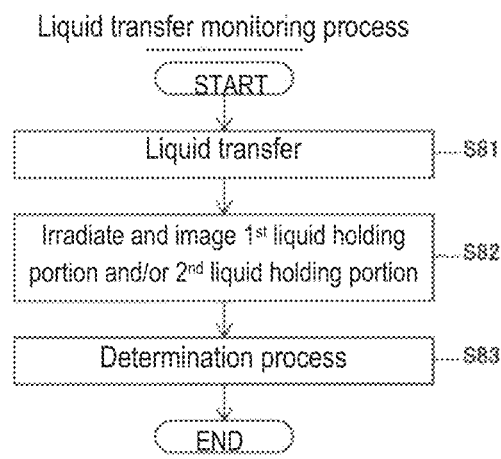
FIG. 21 is a flowchart showing a liquid transfer monitoring process of the sample measuring device.
Figure 22:
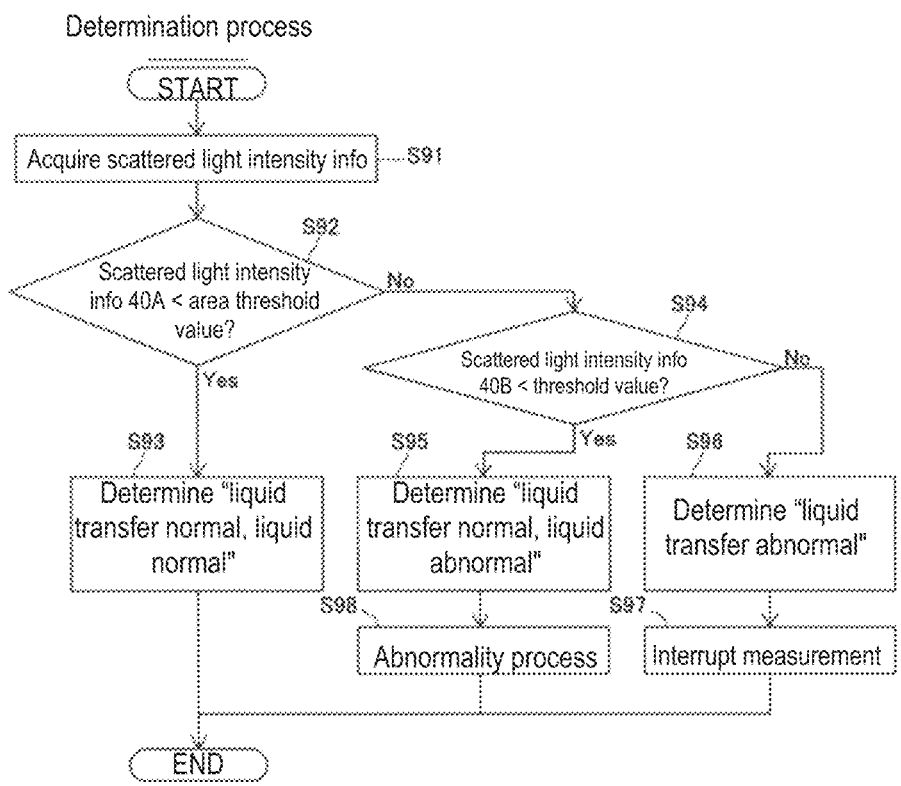
FIG. 22 is a flowchart showing details of the determination process of FIG. 21.

Specifically, in step S81 of FIG. 21, the control unit 140 causes the rotation mechanism 111 to rotate the cartridge 300 at high speed, and moves the liquid 30 from the passage 331 to the liquid chamber 311 by centrifugal force. At this time, the excess liquid 30 exceeding the predetermined amount moves to the liquid chamber 312. In the liquid chamber 311, the liquid 30 also is separated into a liquid component that is plasma and a solid component such as blood cells by the centrifugal force. The separated plasma moves into the passage 333 by capillary action and fills the passage 333.

In step S82, the control unit 140 captures an image of the monitoring target after centrifugation. The monitoring targets are the liquid chamber 311, the liquid chamber 312, and the connection portion 333b of the passage 333. When the liquid chamber 311 is to be monitored, the passage 331 is the first liquid holding portion 21 and the liquid chamber 311 is the second liquid holding portion 22. When the liquid chamber 312 is to be monitored, the liquid chamber 311 is the first liquid holding portion 21, and the liquid chamber 312 is the second liquid holding portion 22. As shown in FIGS. 18 and 19, when the connection portion 333b is to be monitored, the liquid chamber 311 is the first liquid holding portion 21, and the connection portion 333b is the second liquid holding portion 22.

The control unit 140 causes the rotation mechanism 111 to rotate the cartridge 300 to move the first liquid holding portion 21 and/or the second liquid holding portion 22 to the imaging range 132. The first liquid holding portion 21 and/or the second liquid holding portion 22 is positioned directly below the imaging unit 131. The control unit 140 causes the illumination unit 120 to emit light. The control unit 140 causes the imaging unit 131 to acquire the image 410 of the inner bottom surface 24. In step S83, the control unit 140 determines whether there is a liquid transfer abnormality to the liquid chamber 311 based on the image 410.

In step S63 of FIG. 20, the control unit 140 performs a process of transferring the plasma in the passage 333 and the reagent in each storage unit 341.

Specifically, in step S81 of FIG. 21, the control unit 140 causes the rotation mechanism 111 to rotate the cartridge 300, and positions the sealing body 350 of the storage unit 341 directly below the opening unit 162. The control unit 140 drives the opening unit 162 to open the sealing body 350 of the storage unit 341. The control unit 140 repeatedly performs the opening operation to open the sealing bodies 350 of the six storage units 341 located in the radial direction of the reaction chambers 314 to 319. The control unit 140 causes the rotation mechanism 111 to rotate the cartridge 300 and transfers the liquid by centrifugal force. That is, the plasma in the passage 333 is transferred from the passage 333 to the reaction chamber 314. The R1 reagent is transferred to the reaction chamber 314. The R3 reagent is transferred to the reaction chamber 315. The cleaning liquid is sent to each of the reaction chambers 316 to 318. The R4 reagent is sent to the reaction chamber 319.

In step S82, the control unit 140 causes the rotation mechanism 111 to rotate the cartridge 300 to move the first liquid holding portion 21 and/or the second liquid holding portion 22 to the imaging range 132, and the imaging unit 131 acquires an image 410. For example, when the reaction chamber 314 is to be monitored, the passage 333 is the first liquid holding portion 21 and the reaction chamber 314 is the second liquid holding portion 22. The control unit 140 acquires the image 410 of the connection portion 333b that is the first liquid holding portion 21 after the liquid has been sent. In the image 410 of the connection portion 333b after the liquid transfer, if the area information of the region in which the liquid 30 exists is within the allowable range, it can be confirmed that substantially the entire amount of the liquid 30 quantified in the passage 333 is transferred to the reaction chamber 314. In this way the control unit 140 determines, based on the image 410, whether there is a liquid transfer abnormality to each of the second liquid holding portions 22.

After the transfer of the liquid, the control unit 140 performs a process of stirring the liquid in the chamber 310. That is, the control unit 140 causes the rotation mechanism 111 to rotate the cartridge 300 and repeats acceleration and deceleration during rotation. As a result, plasma, R1 reagent, and R2 reagent are mixed in the reaction chamber 314.

The R1 reagent contains a capture substance that binds to the test substance. The capture substance includes, for example, an antibody that binds to the test substance. The antibody is, for example, a biotin-conjugated HBs monoclonal antibody. The R2 reagent contains magnetic particles. The magnetic particles are, for example, streptavidin-bonded magnetic particles whose surface is coated with avidin. When step S63 is performed, the test substance and the R1 reagent are bound by an antigen-antibody reaction. Then, due to the reaction between the antigen-antibody reactant and the magnetic particles, the test substance bound to the capturing substance of the R1 reagent binds to the magnetic particles via the capturing substance. As a result, a complex in which the test substance and the magnetic particles are bound is produced.

Next, in step S64, the control unit 140 transfers the complex in the reaction chamber 314 from the reaction chamber 314 to the reaction chamber 315.

During the transfer of the complex, the control unit 140 drives the magnet drive unit 161 to bring the magnet 161a closer to the cartridge 300 and collect the complex that disperses in the reaction chamber 314. The control unit 140 combines the radial movement of the magnet 161a driven by the magnet drive unit 161 and the circumferential movement of the cartridge 300 by the rotation mechanism 111 to move the complex along the passage 335. That is, the control unit 140 moves the complex from the inside of the reaction chamber 314 to the reaction chamber 315 in the order of radial inward movement of the route PT1, circumferential movement of the route PT2, and radial outward movement of the route PT3 in FIG. 16. The control unit 140 performs the stirring process after moving the complex. Since the transfer of the complex to each of the reaction chambers 315 to 319 is performed by the same method, detailed description will be omitted.

By transferring the complex to the reaction chamber 315, the complex produced in the reaction chamber 314 and the R3 reagent are mixed in the reaction chamber 315. Here, the R3 reagent contains a labeling substance. The labeling substance includes a capture substance that specifically binds to the test substance and a label. For example, the labeling substance is a labeled antibody in which the antibody is used as a capture substance. As a result of step S64, a complex in which the test substance, the capture antibody, the magnetic particles MP, and the labeled antibody are bound is produced in the reaction chamber 315.

In step S65, the control unit 140 transfers the complex in the reaction chamber 315 from the reaction chamber 315 to the reaction chamber 316. In this way, the complex produced in the reaction chamber 315 and the cleaning liquid are mixed in the reaction chamber 316. When the stirring process is performed in step S65, the complex and the unreacted substance are separated in the reaction chamber 316. That is, in the reaction chamber 316, unreacted substances are removed by cleaning.

In step S66, the control unit 140 transfers the complex in the reaction chamber 316 from the reaction chamber 316 to the reaction chamber 317. In this way unreacted substances are removed by cleaning in the reaction chamber 317.

In step S67, the control unit 140 transfers the complex in the reaction chamber 317 from the reaction chamber 317 to the reaction chamber 318. In this way unreacted substances are removed by cleaning in the reaction chamber 318.

In step S68, the control unit 140 transfers the complex in the reaction chamber 318 from the reaction chamber 318 to the reaction chamber 319. In this way, the complex produced in the reaction chamber 314 and the R4 reagent are mixed in the reaction chamber 319. Here, the R4 reagent is a reagent for dispersing the complex. The R4 reagent is, for example, a buffer solution. When the stirring process is performed in step S68, the complex generated in the reaction chamber 314 is dispersed in the R4 reagent in the reaction chamber 319.

In step S69, the control unit 140 transfers the R5 reagent to the reaction chamber 319. Specifically, the control unit 140 opens the sealing body 350 of the storage unit 342, similarly to step S63. The control unit 140 causes the rotation mechanism 111 to rotate the cartridge 300, and transfers the R5 reagent accommodated in the storage unit 342 to the reaction chamber 319 by centrifugal force. In the reaction chamber 319, the R5 reagent is further mixed with the mixed liquid generated in step S68.

Here, the R5 reagent comprises a luminescent substrate that produces light upon reaction with the labeled antibody bound to the complex. In step S69, a measurement sample is prepared. The measurement sample in the reaction chamber 319 emits chemiluminescence when the labeling substance bound to the complex reacts with the luminescent substrate.

In step S70, the control unit 140 causes the rotation mechanism 111 to rotate the cartridge 300 to position the reaction chamber 319 at the detection position 146 immediately above the detector 145a. The detector 145a detects the light emitted from the reaction chamber 319.

In step S71, the control unit 140 performs the measurement process related to immunity based on the light detected by the detector 145a. The measurement unit 145 counts photons and outputs a count value. The control unit 140 measures the presence/absence and amount of the test substance based on the count value output from the measurement unit 145 and the calibration curve, and generates a measurement result.

When the measurement result is obtained, in step S72 the control unit 140 associates the measurement result with the information read from the identifier 400 and the measurement execution date and time at the time of measurement, and records the measurement result data 405 in the storage unit 141. The control unit 140 also transmits the measurement result data 405 to the terminal 500 and the server 600 via the communication unit 142.

With the above, the measurement operation of the sample measuring device 100 is completed.

Determination Process

Next, the determination process in step S83 of FIG. 21 will be described with reference to FIG. 21.

First, in step S91, the control unit 140 acquires the information 40 on the scattered light intensity from the acquired image 410. The content of the analysis differs depending on the monitoring target to be imaged. Here, the liquid transfer monitoring in the above-mentioned connection portion 333b will be described as an example. The control unit 140 acquires the information 40A related to the scattered light intensity and the information 40B related to the scattered light intensity.

In step S92, the control unit 140 determines whether the information 40A related to the scattered light intensity is equal to or less than the area threshold value. When the information 40A related to the scattered light intensity is equal to or smaller than the area threshold value, the control unit 140 proceeds to step S93, determines "no liquid transfer abnormality, no liquid abnormality", and ends the determination process. When the information 40A related to the scattered light intensity is larger than the area threshold, the control unit 140 advances the process to step S94.

In step S94, the control unit 140 determines whether the information 40B related to the scattered light intensity is less than or equal to the threshold value of the sum of the index values. When the information 40B related to the scattered light intensity is less than or equal to the threshold value, the control unit 140 proceeds to step S95 and determines "no liquid transfer abnormality, liquid abnormality". When the information 40B relayed to the scattered light intensity is larger than the threshold value, the control unit 140 proceeds to step S96 and determines that "liquid transfer abnormality".

When it is determined in step S96 that there is a "liquid transfer abnormality", the control unit 140 stops the measurement in step S97. The control unit 140 suspends the processing operation and suspends the measurement. The control unit 140 also notifies the user that the error has occurred by the notification unit 143. If the measurement is stopped due to an abnormality, no measurement result is generated.

Figures 23, 24:
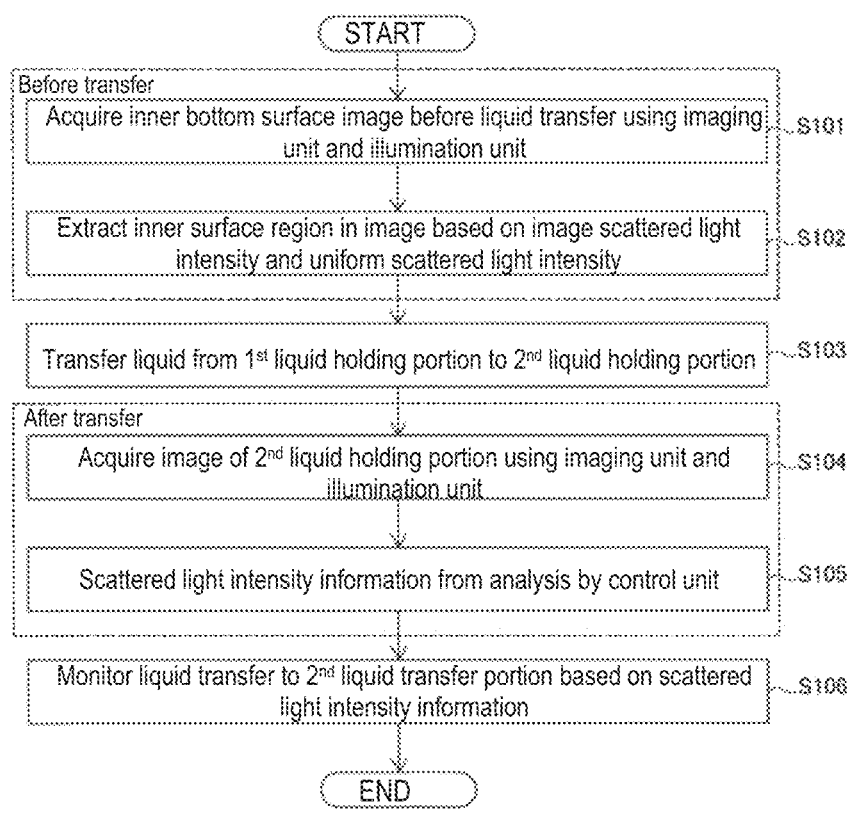
FIG. 23 is a diagram showing an example of the abnormality process of FIG. 22.
FIG. 24 is a flowchart showing a liquid transfer monitoring process according to a modification.

When "no liquid transfer abnormality, liquid abnormality" is determined in step S95, the control unit 140 executes abnormality processing in step S98. Specific examples (1) to (3) of the abnormality processing are shown in FIG. 23.

(1) The control unit 140 stops the measurement. That is, the control unit 140 performs the same process as step S97. In this case, the measurement result is not output.

(2) The control unit 140 notifies the user during measurement. The control unit 140 notifies the user that an abnormality is found in the liquid 30 while continuing the measurement operation. The control unit 140 notifies the user of the abnormality by, for example, the notification unit 143. The control unit 140 causes the display unit 510 of the terminal 500 to display that an abnormality has occurred.

(3) The control unit 140 performs a process of displaying on the display unit 510 that the measurement result is abnormal. For example, when chyle is found in plasma, control unit 140 records flag information indicating that chyle is found. When the flag information is recorded at the time the measurement result is acquired in step S71, the control unit 140 generates the measurement result data 405 including the information indicating that chyle is identified in the measurement result. In step S72, the control unit 140 transmits the generated measurement result data 405 to the terminal 500 and causes the display unit 510 of the terminal 500 to display measurement result data.

As described above, when an abnormality is determined (S95, S96), the control unit 140 executes steps (S97, S98) to suspend the measurement, notify the user during the measurement, or display that the measurement result is abnormal. In this way, when there is an abnormality in the liquid transfer, the user can know that there is an abnormality in the liquid transfer.

The determination process of step S83 is performed as described above.

Note that in the above measurement operation, chemiluminescence is light emitted by utilizing energy from a chemical reaction, for example, light emitted when a molecule is excited into a excited state by the chemical reaction and then returns to a ground state. Chemiluminescence can be generated by, for example, a reaction between an enzyme and a substrate, an electrochemical stimulus is given to a labeling substance, a LOCI method (Luminescent Oxygen Channeling Immunoassay), or bioluminescence. In the first embodiment, any chemiluminescence may occur. A complex may be formed by binding a substance that is excited by fluorescence when irradiated with light having a predetermined wavelength and a test substance. In this case, a light source for irradiating the reaction chamber 319 with light is arranged. The photodetector detects the fluorescence excited from the substance bound to the complex by the light from the light source.

Note that the magnetic particles may be particles that contain a magnetic material as a base material, and may be used for ordinary immunoassay. For example, magnetic particles using Fe2O3 and/or Fe3O4, cobalt, nickel, filite, magnetite or the like as the base material can be used. The magnetic particles also may be coated with a binding substance for binding to the test substance or may be bound to the test substance via a capture substance for binding the magnetic particles and the test substance. The capture substances are magnetic particles and antigens or antibodies which mutually bind to the test substance.

The capture substance is not particularly limited insofar as it specifically binds to the test substance. For example, a capture substance may bind to a test substance by an antigen-antibody reaction. More specifically, the capture substance may be an antibody, but when the test substance is an antibody, the capture substance may be an antigen of the antibody. When the test substance is a nucleic acid, the capture substance may be a nucleic acid complementary to the test substance. As the label contained in the labeling substance, for example, an enzyme, a fluorescent substance, a radioactive isotope and the like can be mentioned. Examples of the enzyme include alkaline phosphatase (ALP), peroxidase, glucose oxidase, tyrosinase, acid phosphatase and the like. When performing electrochemiluminescence as the chemiluminescence, the label is not particularly limited insofar as it is a substance that emits light by electrochemical stimulation, for example, a ruthenium complex can be mentioned. Examples of fluorescent substances include fluorescein isothiocyanate (FITC), green fluorescent protein (GFP), luciferin and the like. Examples of radioactive isotopes include 125I, 14C, 32P and the liked.

When the label is an enzyme, a known luminescent substrate may be appropriately selected according to the enzyme to be used as the luminescent substrate for the enzyme. Examples of useful luminescent substrates when alkaline phosphatase is used as an enzyme include chemiluminescent substrates such as CDP-Star (registered trademark), (4-Chloro-3-(methoxyspiro[1,2-dioxetane-3,2'-(5'-chloro)triculo[3.3.13,7]decane]-4-yl)phenylphosphate disodium), CSPD (registered trademark) (3-(4-methoxyspiro[1,2-dioxetane-3,2-(5'-chloro)tricyclo[3.3.1.13,7]decane]-4-yl)phenyl disodium phosphate) and the like; luminescent substrates such as p-nitrophenyl phosphate, 5-bromo-4-chloro-3-indolyl phosphoric acid (BLIP), 4-nitro blue tetrazolium chloride (NBT), Iodonitrotetrazolium (INT) and the like; fluorescent substrates such as 4-methylum beryphenyl phosphate (4MUP) and the like; and chromogenic substrates such as 5-bromo-4-chloro-3-indolyl phosphoric acid (BLIP), disodium 5-bromo-6-chloro-indo-lyl phosphate, p-nitrophenyl phosphorus and the like.

Modifications

Note that the embodiments disclosed herein are examples in all respects and are not restrictive. The scope of the present invention is indicated not by the description of the above embodiments but by the scope of the claims, and includes meanings equivalent to the claims and all changes within the scope thereof.

For example, in FIG. 18, a region in the image in which the connection portion 333*b* (that is, the inner surface 23) in the image is known from the design information, and the region extraction process is performed based on the known information to obtain the extracted images 411*b* and 412*b*; the present invention is not limited to this, however. The area of the inner surface 23 shown in the image may be detected regardless of the known information.

That is, in the modified example shown in FIG. 24, the image analysis includes a process (refer to step S102) of extracting a region 440 (refer to FIG. 25) of the inner surface in the image 430 (refer to FIG. 25) based on the scattered light intensity and the uniformity of the scattered light intensity. Then, the information 40 related to the scattered light intensity is acquired from the extracted region 440 of the inner surface. In this way, even if the position of the liquid holding portion 20 slightly deviates from the design value due to an error factor, the region 440 of the inner surface in the actual image 430 can be acquired, and thus highly accurate image analysis becomes possible. In the actual image 430, there is a concern that noise 441 (see FIG. 25) due to light from a portion other than the inner surface 23 may exist. In contrast, the position of the inner surface 23 including the noise 441 can be suitably detected based on the uniformity of the scattered light intensity from the significantly reduced dispersion of the scattered light intensity of the region 440 of the inner surface by the irregularity of the inner surface 23 on the one hand, and the reduced dispersion of the scattered light intensity in the noise 441.

Specifically, in step S101 of FIG. 24, the control unit 140 acquires the image 430 (refer to FIG. 25) of the inner surface 23 using the imaging unit 131 and the illumination unit 120 before the liquid 30 is transferred to the second liquid holding portion 22. At this time, the position of the inner surface 23 in the image 430 may be slightly deviated from the design value due to a shape error of the cartridge 300, an error in rotation position control by the rotation mechanism 111, or the like.

In step S102, the control unit 140 executes a process of extracting the region 440 on the inner surface in the image 430 based on the scattered light intensity and the uniformity of the scattered light intensity. The details of the process of extracting the region 440 on the inner surface will be described with reference to FIG. 25.

Figure 25:
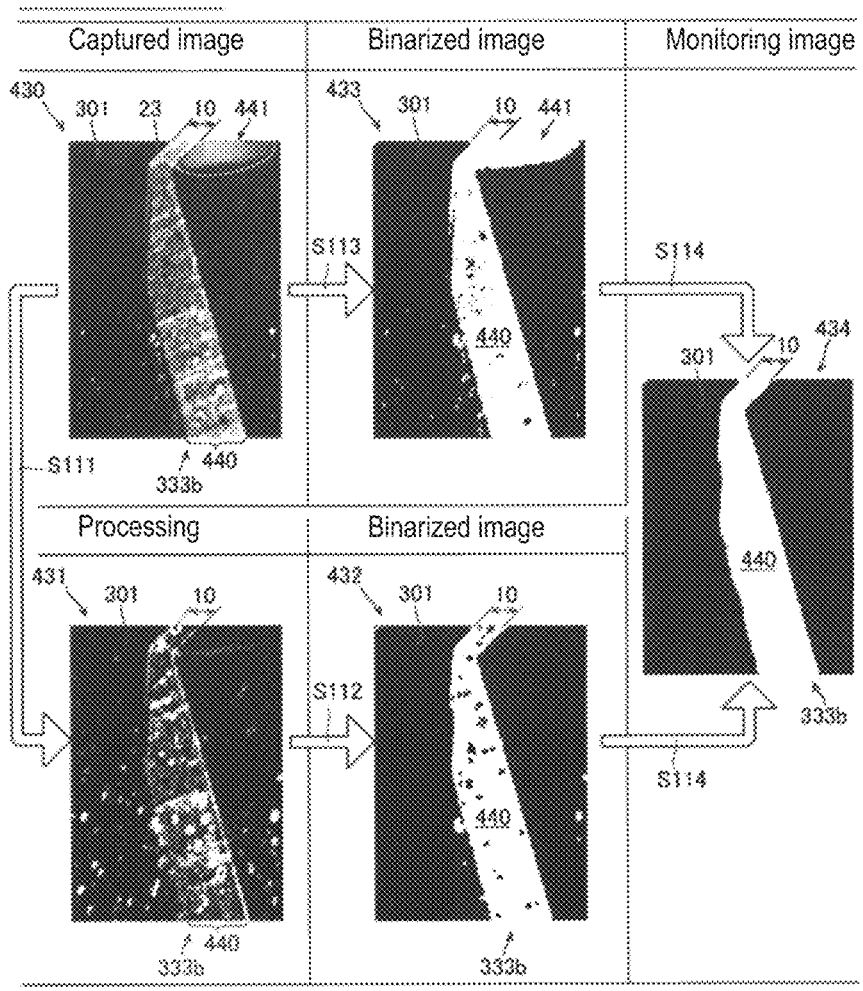
FIG. 25 is a diagram illustrating a process of extracting an inner surface area in an image.
Figure 26:
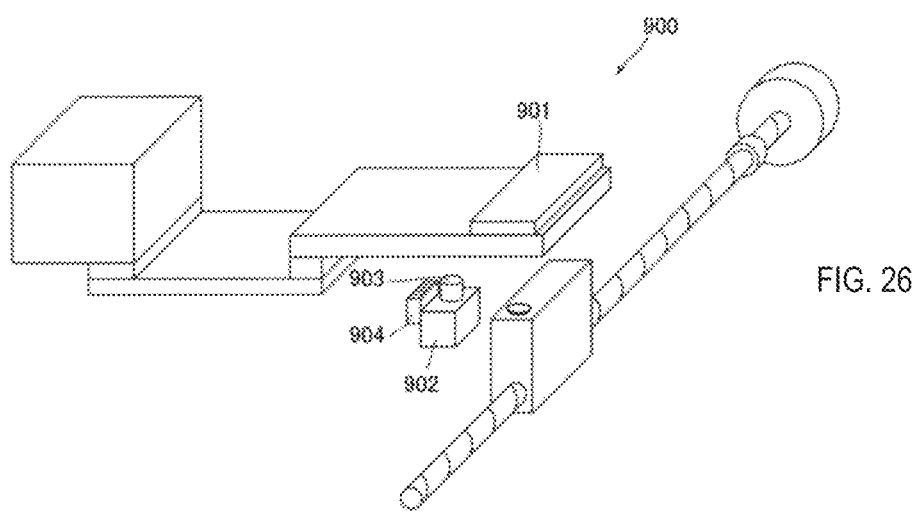
FIG. 26 is a diagram illustrating a conventional technique.

Here, the image 430 may include noise 441 due to the surface reflection of the substrate 301 outside the flow path 10 in which the inner surface 23 is formed. FIG. 25 shows an example in which the noise 441 surrounded by a dotted line is detected on the surface of the substrate near the tip of the connecting portion 333*b*. The presence of the noise 441 makes it difficult to distinguish the inner surface 23 from the substrate surface simply based on the scattered light intensity.

Therefore, in the example of FIG. 25, the region 440 of the irregular inner surface and the outside of the flow channel 10 are distinguished by the uniformity of the scattered light intensity. The uniformity of scattered light intensity means that the difference in pixel value between the pixel of interest and its peripheral pixels is small. The substrate surface on which the noise 441 is detected is a smooth surface having a surface roughness smaller than that of the irregular inner surface 23. Therefore, in the area of the noise 441 shown in FIG. 25, the pixel value is more uniform than in the region 440 on the inner surface.

Here, a coefficient of variation (CV) is adopted as an example of an index for evaluating the uniformity of scattered light intensity. In step S111, the control unit 140 performs the CV filter process on the image 430 to acquire the variation coefficient for each pixel in the image 430. The coefficient of variation is calculated from each pixel value in the pixel group including the pixel of interest and its peripheral pixels. The variation coefficient CV of the pixel of interest is CV=(standard deviation of pixel value of pixel group)/(average value of pixel value of pixel group). In the processed image 431 after the CV filter processing, the pixel value of each pixel represents the value of the variation coefficient. In the processed image 431, the higher the pixel value, the more uneven the scattered light intensity, and the lower the pixel value, the more uniform the scattered light intensity. In the region 440 on the inner surface of the image 430, the scattered light intensity has a large variation, and thus the pixel value in the processed image 431 is high. On the other hand, in the area of the noise 441, since the scattered light intensity has a small variation, the pixel value in the processed image 431 is low.

The control unit 140 executes step S112 of performing binarization processing on the processed image 431 by the CV filter. The binarization threshold is set between the pixel value range in the region 440 on the inner surface and the pixel value range in the area of the noise 441. By step S112, the binarized image 432 in which the high pixel value area including the region 440 on the inner surface is white (=255, upper limit value) and the area of the noise 441 is black (=0, lower limit value) is obtained.

In addition to the processed image 431, the control unit 140 also performs the binarization process of the image 430 in step S113 to acquire the binarized image 433 based on the scattered light intensity. The binarization process in step S113 is the same as the binarization process shown in FIG. 18, and thus description thereof will be omitted. Since the binarized image 433 is simply binarized based on the scattered light intensity, when the image 430 includes the noise 441, not only the region 440 on the inner surface but also the region of the noise 441 is also white (=255).

In step S114, the control unit 140 acquires a region image 434 extracted from the region 440 on the inner surface based on the binarized image 433 derived from the scattered light intensity and the binarized image 432 derived from the coefficient of variation. Specifically, the control unit 140 obtains a logical product (AND) of the binarized image 433 and the binarized image 432. In this way only the region in which the pixel values of the binarized image 433 and the binarized image 432 are common (=255) becomes white (=255) in the region image 434.

As a result of the logical operation, the region of the noise 441 existing only in the binarized image 433 is removed, and only the inner surface region 440 (that is, the inside of the flow channel 10) that is commonly present in the binarized image 433 and the binarized image 432 is extracted as an area having a white (=255) pixel value. Note that, to be more precise, when a logical product is calculated between the binarized image 433 and the binarized image 432 of FIG. 25, black regions scattered inside the inner surface region 440 remain in the region image 434. The control unit 140 executes a known correction process such as a morphological conversion to remove the scattered black regions, and acquires a region image 434 shown in FIG. 25. The white area of the area image 434 becomes the region 440 on the inner surface.

Through the above steps S111 to S114, the control unit 140 extracts the region 440 on the inner surface. The control unit 140 acquires the information 40 on the scattered light intensity from the extracted inner surface region 440.

That is, as shown in FIG. 24, after extracting the region 440 on the inner surface, the control unit 140 performs the process of transferring the liquid of the first liquid holding portion 21 to the second liquid holding portion 22 in step S103. In step S104, the control unit 140 acquires the image 410 (see FIG. 18) of the second liquid holding portion 22 by the imaging unit 131 and the illumination unit 120 after the liquid 30 is transferred to the second liquid holding portion 22. Then, in step S105, the control unit 140 extracts the range specified by the region 440 acquired in step S102 from the processed image 412a of the image 410 to acquire an extracted image 412b (see FIG. 18), and acquire the information 40 related to the light intensity. In step S106, the control unit 140 monitors the liquid transfer to the second liquid holding portion 22 based on the information 40 related to the scattered light intensity. The processes of steps S103 to S106 are as already described, and thus detailed description thereof will be omitted.

What is claimed is:

1. A method for monitoring a transfer state of a liquid used in a sample measuring device transferred in a flow path having at least two liquid holding portions, the method comprising:
    transferring the liquid held in a first liquid holding portion to a second liquid holding portion connected to the first liquid holding portion;
    completing transfer of the liquid from the first liquid holding portion to the second liquid holding portion;
    acquiring information related to scattered light intensity obtained by irradiating light on an inner surface having irregularities of at least one of the first liquid holding portion and the second liquid holding portion after the transfer of the liquid is completed and the flow of liquid has stopped; and
    monitoring a state of the liquid transferred to the second liquid holding portion based on the information related to the scattered light intensity.

2. The method according to claim 1, wherein
    in the step of acquiring information related to the scattered light intensity, light is irradiated on the inner surface having irregularities after transfer of the liquid is completed.

3. The method according to claim 2, wherein
    the information related to the scattered light intensity is acquired by a photodetector detecting scattered light, and a controller connected to the photodetector analyzing a signal from the photodetector.

4. The method according to claim 3, wherein
    the photodetector comprises an imaging unit having a sensor; and
    analysis performed by the controller is an image analysis.

5. The method according to claim 4, wherein
    the inner surface is an inner bottom surface of the at least one of the first liquid holding portion and the second liquid holding portion.

6. The method according to claim 5, wherein
    in the step of acquiring information related to the scattered light intensity, light is obliquely irradiated on the inner surface and the scattered light is detected by the imaging unit at a position above the inner surface.

7. The method according to claim 4, wherein
    the image analysis is locally performed on an area including at least one of the first liquid holding portion and the second liquid holding portion.

8. The method according to claim 4, wherein
    the image analysis comprises a binarization process that divides an image captured by the photodetector into a region in which the scattered light intensity is less than a binarization threshold value and a region in which the scattered light intensity is equal to or greater than the binarization threshold value.

9. The method according to claim 8, wherein
    the information relating to the scattered light intensity is area information of the region in which the scattered light intensity is equal to or greater than the binarization threshold value obtained by the binarization process.

10. The method according to claim 9, wherein
    the step of monitoring the liquid transfer comprises determining the presence or absence of an anomaly in the liquid transfer to the second liquid holding portion based on a comparison result of comparing, after the flow of liquid has stopped, an area threshold value and an area value of the region in which the scattered light intensity is equal to or greater than the binarization threshold value.

11. The method according to claim 4, wherein
    the image analysis comprises a process of calculating an index value indicating a dispersion in scattered light intensity in a region in which scattered light is detected; and
    the information related to scattered light intensity comprises a total sum of the index values in the region.

12. The method according to claim 11, wherein
    in the step of monitoring the liquid transfer, the total sum of the index values is compared with a threshold value of the total sum of the index values, and whether there is an abnormality in the liquid transferred to the second liquid holding portion is determined based on a result of the comparison.

13. The method according to claim 12, wherein
    the liquid is plasma, and the abnormality in the liquid is chyle.

14. The method according to claim 1, wherein
    presence or absence of a liquid transfer abnormality is determined by comparing information related to scattered light intensities acquired before and after the liquid is transported.

15. The method according to claim 10, further comprising:
    a step of stopping measurement, notifying a user during the measurement, or displaying a message that there is an abnormality in a measurement result when the anomaly is a liquid transfer abnormality.

16. The method according to claim 4, wherein
    image analysis comprises a process of extracting a region of the inner surface in an image based on scattered light intensity and a uniformity of the scattered light intensity; and
    the information related to the scattered light intensity is acquired from the extracted region of the inner surface.

17. A sample measuring device that transfers a liquid to a flow path having at least two liquid holding portions and performs measurement using the liquid, the measuring device comprising:

a liquid feeding pump that applies an external force to the liquid held in a first liquid holding portion and transfers the liquid to a second liquid holding portion connected to the first liquid holding portion;

a light source that irradiates light on an irregular inner surface of at least one of the first liquid holding portion and the second liquid holding portion;

a photodetector for detecting scattered light originating from light irradiated on the irregular inner surface;

a controller configured to acquire information related to scattered light based on signals from the photodetector, and determine a presence or absence of a liquid within the first liquid holding portion, the second liquid holding portion, or both, based on the information related to the scattered light; and a measurement unit comprising the photodetector that performs measurement using the liquid, wherein the controller is configured to direct transfer of the liquid from the first liquid holding portion to the second liquid holding portion, cause the light source to irradiate light on the irregular inner surface after the transfer of the liquid from the first liquid holding portion to the second liquid holding portion is completed and flow of the liquid has stopped, and determine anomalies resulting from the transfer of the liquid from the first liquid holding portion to the second liquid holding portion.

18. The sample measuring device according to claim 17, wherein the controller is configured to monitor the liquid transfer to the second liquid holding portion by determining the presence or absence of the liquid based on a scattered light intensity of the scattered light.

19. The sample measuring device according to claim 18, wherein the photodetector comprises an imaging unit having a sensor; and the controller is further configured to acquire the scattered light intensity by image analysis.

20. The method according to claim 1, further comprising determining an abnormality occurred in the transfer of the liquid according to the acquired information related to scattered light intensity.

* * * * *